(12) United States Patent
Harms et al.

(10) Patent No.: US 10,569,024 B2
(45) Date of Patent: Feb. 25, 2020

(54) ASSEMBLY FOR A DRUG DELIVERY DEVICE AND DRUG DELIVERY DEVICE

(71) Applicant: Sanofi-Aventis Deutschland GMBH, Frankfurt am Main (DE)

(72) Inventors: Michael Harms, Frankfurt am Main (DE); Heiko Muller, Stuttgart (DE); Joachim Keitel, Esslingen (DE); Hebert Bechtold, Denkingen (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 458 days.

(21) Appl. No.: 14/917,360

(22) PCT Filed: Sep. 17, 2014

(86) PCT No.: PCT/EP2014/069752
§ 371 (c)(1),
(2) Date: Mar. 8, 2016

(87) PCT Pub. No.: WO2015/040039
PCT Pub. Date: Mar. 26, 2015

(65) Prior Publication Data
US 2016/0213852 A1 Jul. 28, 2016

(30) Foreign Application Priority Data
Sep. 23, 2013 (EP) .................................... 13185478

(51) Int. Cl.
*A61M 5/315* (2006.01)
(52) U.S. Cl.
CPC .... *A61M 5/31541* (2013.01); *A61M 5/31551* (2013.01); *A61M 5/31558* (2013.01); *A61M 5/31575* (2013.01); *A61M 5/31585* (2013.01)

(58) Field of Classification Search
CPC ...................... A61M 5/31541; A61M 5/31551
See application file for complete search history.

(56) References Cited

U.S. PATENT DOCUMENTS

| 533,575 | A | 2/1895 | Wilkens |
| 4,865,591 | A | 9/1989 | Sams |

(Continued)

FOREIGN PATENT DOCUMENTS

| CA | 2138528 | 2/1994 |
| CA | 2359375 | 7/2000 |

(Continued)

OTHER PUBLICATIONS

International Search Report and Written Opinion in International Application No. PCT/EP2014/069752, dated Mar. 5, 2015, 16 pages.

(Continued)

*Primary Examiner* — Rebecca E Eisenberg
*Assistant Examiner* — Tasnim Mehjabin Ahmed
(74) *Attorney, Agent, or Firm* — Fish & Richardson P.C.

(57) ABSTRACT

An assembly includes a cartridge containing doses of a drug and a piston rod adapted and arranged to expel drug from the cartridge, the piston rod including a thread. The assembly further includes a nut member adapted and arranged to be rotated with respect to the piston rod about a rotational axis. The assembly further comprises a last dose stop mechanism adapted including at least one first interaction member and at least one second interaction member provided by the piston rod and at least one first stop member and at least one second stop member provided by the nut member. The interaction members and the stop members are configured to mechanically cooperate with one another such that further relative movement of the nut member and the piston rod for setting a dose of the drug is prevented.

19 Claims, 13 Drawing Sheets

(56) References Cited

U.S. PATENT DOCUMENTS

Figures 1A, 1B:
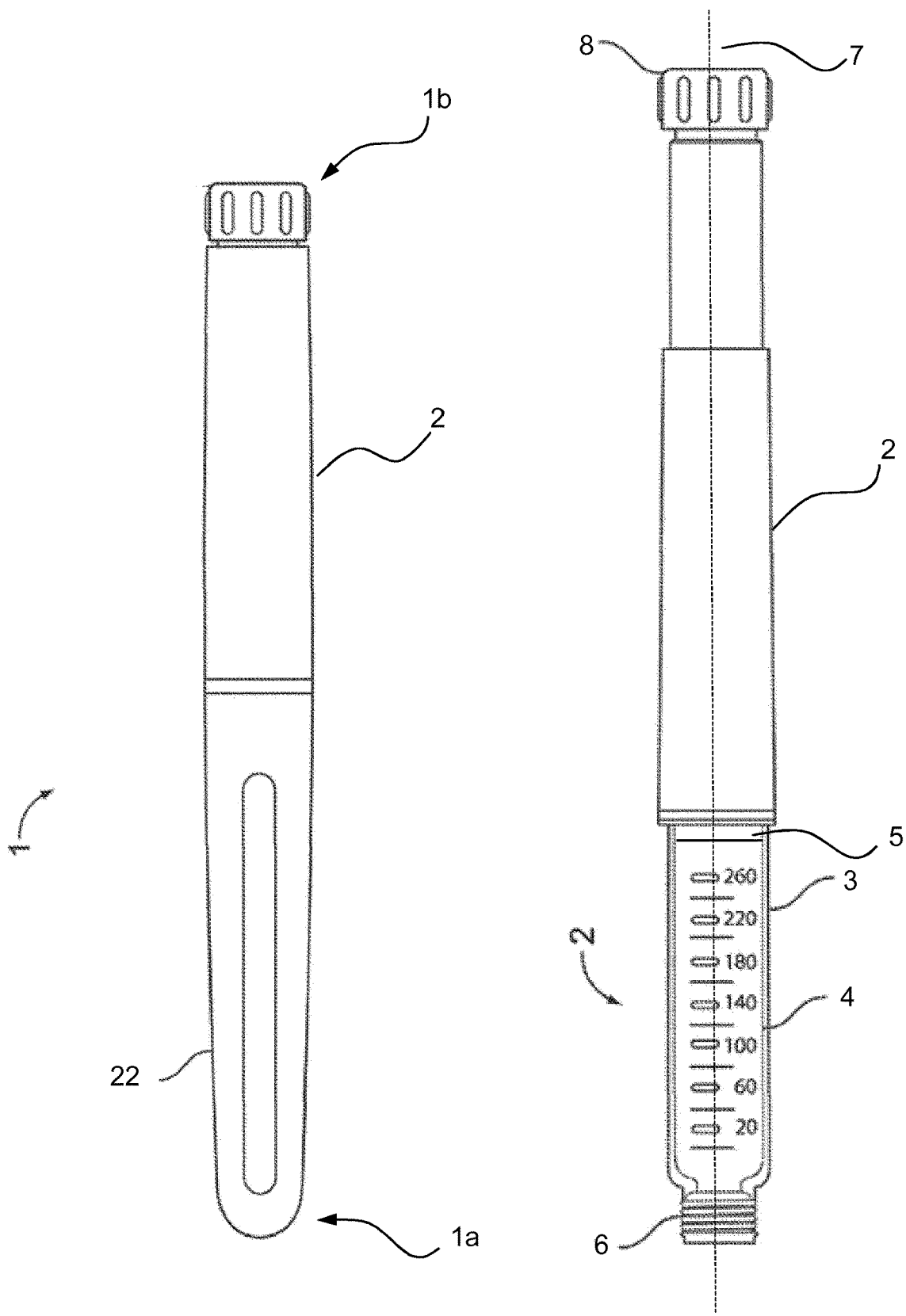

| | | | |
|---|---|---|---|
| 5,092,842 A | 3/1992 | Bechtold | |
| 5,226,895 A | 7/1993 | Harris | |
| 5,226,896 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,391,157 A | 2/1995 | Harris | |
| 5,378,233 A | 3/1995 | Haber | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman | |
| 5,851,079 A | 12/1998 | Horstman | |
| 5,921,966 A | 7/1999 | Bendek et al. | |
| 5,957,896 A | 9/1999 | Bendek | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman | |
| 6,613,023 B2 | 9/2003 | Kirchhofer | |
| 6,699,224 B2 | 3/2004 | Kirchhofer | |
| 6,932,794 B2 | 8/2005 | Giambattista | |
| 6,936,032 B1 | 8/2005 | Bush, Jr. et al. | |
| 7,169,132 B2 | 1/2007 | Bendek | |
| 7,241,278 B2 | 7/2007 | Moller | |
| 7,678,084 B2 | 3/2010 | Judson | |
| 8,187,233 B2 | 5/2012 | Harms et al. | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0097883 A1 | 5/2004 | Roe | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2006/0114396 A1 | 11/2006 | Novo et al. | |
| 2007/0016143 A1 | 1/2007 | Miller et al. | |
| 2009/0275916 A1 | 11/2009 | Harms et al. | |
| 2010/0268171 A1* | 10/2010 | Moller | A61M 5/31551 604/246 |
| 2011/0319835 A1 | 12/2011 | Burren et al. | |
| 2012/0165751 A1* | 6/2012 | Plumptre | A61M 5/31551 604/207 |
| 2012/0265151 A1 | 10/2012 | Nzike et al. | |
| 2015/0018772 A1* | 1/2015 | Schenker | A61M 5/20 604/189 |

FOREIGN PATENT DOCUMENTS

| | | |
|---|---|---|
| CH | 703909 | 4/2012 |
| CN | 101854968 | 10/2010 |
| CN | 102281909 | 12/2011 |
| EP | 0496141 | 7/1992 |
| EP | 0897729 | 2/1999 |
| EP | 0937471 | 8/1999 |
| EP | 0937476 | 8/1999 |
| EP | 1776975 | 4/2007 |
| GB | 0304822.0 | 3/2003 |
| GB | 0304823.8 | 11/2017 |
| WO | WO 93/07922 | 4/1993 |
| WO | WO 93/24160 | 12/1993 |
| WO | WO 1999/038554 | 8/1999 |
| WO | WO 2001/010484 | 2/2001 |
| WO | WO 02/030495 | 4/2002 |
| WO | WO 02/092153 | 11/2002 |
| WO | WO 03/080160 | 10/2003 |
| WO | WO 2006/084876 | 8/2006 |
| WO | WO2006/114396 | 11/2006 |
| WO | WO2008/058666 | 5/2008 |
| WO | WO2009/039851 | 4/2009 |
| WO | WO 2010/066797 | 6/2010 |
| WO | WO 2010/139645 | 12/2010 |

OTHER PUBLICATIONS

International Preliminary Report on Patentability in International Application No. PCT/EP2014/069752, dated Mar. 29, 2016, 11 pages.

Rote Liste, "50. Hypophysen—, Hypothalamushormone, andere regulatorische Peptide u. ihre Hemmstoffe," Chapter 50, ed. 2008, 20 pages.

"Pen-injectors for medical use—Part 1: Pen-injectors—Requirements and test methods," International Standard, reference No. ISO 11608-1:2000(E), first edition Dec. 15, 2000, 32 pages.

"British Standard Specification for Spring Washers for General Engineering and Automobile Purposes—Metric Series," British Standards Institution, BS 4464, May 19, 1969, 14 pages.

* cited by examiner

ASSEMBLY FOR A DRUG DELIVERY DEVICE AND DRUG DELIVERY DEVICE

CROSS-REFERENCE TO RELATED APPLICATIONS

This application is a U.S. national stage application under 35 USC § 371 of International Application No. PCT/EP2014/069752, filed on Sep. 17, 2014, which claims priority to European Patent Application No. 13185478.8, filed on Sep. 23, 2013, the entire contents of which are incorporated herein by reference.

The present disclosure relates to an assembly for a drug delivery device. Furthermore, the present disclosure relates to a drug delivery device.

In a drug delivery device, often, a bung within a cartridge containing a plurality of doses of a drug is displaced by a piston rod. Thereby, a dose of the drug is expelled from the cartridge.

A drug delivery device is described in document WO 2008/058666 A1, for example.

Aspects of the present invention may include an improved drug delivery device.

One aspect relates to an assembly for a drug delivery device. The assembly comprises a cartridge containing a plurality of doses of a drug. The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The assembly further comprises a piston rod. The piston rod may be moveable in an axial direction with respect to a housing of the device. The piston rod may be prevented from rotational movement with respect to the housing. The piston rod is adapted and arranged to expel drug from the cartridge during a dose delivery operation of the assembly. The piston rod comprises a thread. The thread is provided on an outer surface of the piston rod. The thread extends along the outer surface of the piston rod. The assembly further comprises a nut member. The nut member may be formed sleeve-like. The nut member may comprise a ratchet sleeve, for example. The nut member may comprise a circular nut. The nut member is adapted and arranged to mechanically cooperate with the piston rod during a dose setting and a dose delivery operation. The nut member and the piston rod are adapted and arranged to be rotated with respect to one another about a rotational axis during a dose setting operation of the assembly. The rotational axis may be the main longitudinal axis of the device. Preferably, the nut member rotates with respect to the piston rod and the piston rod is secured against rotational movement during dose setting. During the rotation, the nut member is axially displaced along the piston rod from a start position towards an end position with respect to the piston rod due to mechanical cooperation of the nut member with the thread.

The assembly further comprises a last dose stop mechanism. The last dose stop mechanism is adapted and arranged to prevent a user from setting a dose of the drug which exceeds a remaining amount of drug in the cartridge. The last dose stop mechanism comprises at least one first interaction member and at least one second interaction member. The respective interaction member is provided by the piston rod. The interaction members may be formed integrally with the piston rod. The last dose stop mechanism comprises at least one first stop member and at least one second stop member. The respective stop member is provided by the nut member. The stop members may be formed integrally with the nut member.

The first interaction member may be adapted and arranged to mechanically cooperate with the first stop member. The second interaction member may be adapted and arranged to mechanically cooperate with the second stop member. The interaction members and the stop members are configured to mechanically cooperate with one another, in particular to engage with one another, when the nut member is in the end position with respect to the piston rod such that further relative movement of the nut member and the piston rod for setting a dose of the drug is prevented. The end position of the nut member with respect to the piston rod may be defined by mechanical cooperation of the stop features and the interaction features, in particular of the first stop feature with the first interaction member and of the second stop feature with the second interaction member. The displacement distance of the nut member between the start position and the end position may correspond to the amount of drug contained in the cartridge.

The last dose stop mechanism locks the assembly to prevent a further dose setting operation, e.g. until a replacement cartridge was introduced in the device. By means of the last dose stop mechanism, the dose of drug that may be set by a user is limited to less than or equal to the amount of drug remaining in the cartridge. As the nut member and the piston rod each comprise two members adapted and arranged to mechanically cooperate in a last dose stop situation, two separate mechanisms are provided to prevent setting of a dose which exceeds the amount of remaining drug. Thus, a very reliable last dose stop mechanism is provided. In particular, the mechanism may not be overturnable by a user. In this way, setting or dispensing of an underdose of the drug is prevented. Thus, safety of the device is increased. A further advantage of the last dose stop mechanism is that the assembly may be locked in a state during a setting movement. In this way, a user may recognize already during dose setting that the cartridge is empty.

According to one embodiment, the last dose stop mechanism comprises a radial stop mechanism. The first stop member may comprise at least one radial stop face. This means that the first stop member may comprise an edge or a protrusion protruding from the nut member in a radial direction. The first stop member may comprise, for example, two, three or more radial stop faces. The first interaction member may comprise at least one radial stop face. This means that the first interaction member may comprise at least one edge or protrusion protruding from the piston rod in a radial direction. The first interaction member may comprise two, three or more radial stop faces. The radial stop faces of the first stop member and the first interaction member are configured to mechanically cooperate with one another when the nut member is in the end position with respect to the piston rod. Due to mechanical cooperation of the radial stop faces, further rotation of the nut member with respect to the piston rod for setting a dose of drug is prevented.

By means of the radial stop mechanism, a user may not be able to override the last dose stop mechanism even when applying high torque onto the assembly. Thus, provision of a safe device is facilitated.

According to one embodiment, the last dose stop mechanism further comprises an axial stop mechanism. The second stop member may comprise at least one axial stop face. In other words, the second stop member may comprise an edge or a protrusion protruding from the nut member in an axial direction. The second stop member may comprise two, three or more axial stop faces. The second interaction member may comprise at least one axial stop face. This means that the second interaction member may comprise an edge or a protrusion protruding from the piston rod in an axial direction. The second interaction member may comprise two, three or more axial stop faces. The axial stop faces of the second stop member and the second interaction member are configured to mechanically cooperate with one another when the nut member is in the end position with respect to the piston rod. Due to mechanical cooperation of the axial stop faces, further axial movement of the nut member with respect to the piston rod for setting a dose of drug is prevented.

By means of the axial stop mechanism, a user may not be able to override the last dose stop mechanism even when applying high torque onto the assembly. Thus, provision of a safe device is facilitated. The axial stop mechanism and the radial stop mechanism may be configured to be active on parallel such that the relative rotation is stopped by the radial end stop in the same or approximately the same position, i.e. the end position, in which the relative axial movement is stopped by the axial end stop. Thus, a very reliable last dose stop mechanism is provided.

According to one embodiment, the assembly is configured such that a distance between a stop member of the nut member and the corresponding interaction member of the piston rod corresponds to the remaining amount of drug in the cartridge. In other words, an azimuthal distance between the first stop member and the first interaction member and an axial distance between the second stop member and the second interaction member may correspond to the remaining amount of drug in the cartridge, respectively. The azimuthal distance as projected onto the rotational axis may be equal to the axial distance.

According to one embodiment, the assembly is configured such that, for delivering a set dose of the drug, axial and rotational movement of the nut member with respect to the piston rod is prevented. The nut member and the piston rod may be adapted and arranged to move together in an axial direction for expelling drug from the cartridge during a dose delivery operation. In this way, dose accuracy may be increased. Thus, provision of a user friendly drug delivery device may be facilitated.

According to one embodiment, the assembly further comprises a housing. The housing may be shaped tube-like or sleeve-like. The housing may comprise one, two or more tubes. The housing comprises an inner thread. The inner thread may extend at least partly along an inner surface of the housing. The assembly further comprises a dose setting member. The dose setting member may be shaped sleeve-like. The dose setting member is configured to be arranged at least partly within the housing. The dose setting member comprises a first thread. The first thread may be arranged on an outer surface of the dose setting member. The dose setting member is rotatably arranged within the housing due to mechanical cooperation of the inner thread and the first thread. In particular, the dose setting member may be adapted to be rotated with respect to the housing during setting and delivering a dose of the drug. The dose setting member and the housing may have a combined length the magnitude of which before setting a dose corresponds to a predetermined starting length. The combined length may be increasable by the relative rotation of the dose setting member and the housing during a dose setting operation. The combined length may be decreasable, in particular returnable to the predetermined starting length, during a dose delivery operation.

The assembly further comprises a clutch mechanism. The clutch mechanism may comprise at least one toothing, preferably two toothings. The clutch mechanism may be adapted to provide a releasable coupling. The clutch mechanism is adapted and arranged to couple the dose setting member and the nut member during a dose setting operation such that movement of the dose setting member is transferred into axial and rotational movement of the nut member with respect to the piston rod during a dose setting operation. In other words, during dose setting, rotational and axial movement of the dose setting member may be transferred directly into rotational and axial movement of the nut member due to the coupling of nut member and dose setting member.

The clutch mechanism is configured to decouple the dose setting member and the nut member for delivering the set dose such that movement of the nut member with respect to the piston rod during the dose delivery operation is prevented. In other words, during dose delivery, movement of the dose setting member may be transferred only indirectly into movement of the nut member as there is no coupling between the dose setting member and the nut member. In particular, during dose delivery, rotational movement of the dose setting member may not be transferred into rotational movement of the nut member such that there is no relative movement between the nut member and the piston rod when delivering the dose.

The clutch mechanism may be configured such that it decouples the dose setting member and the nut member due to an operation which takes place at a beginning of a dose delivery operation. In particular, when initializing the dose delivery operation, the dose setting member and the nut member may become decoupled. The dose setting member and the nut member may become decoupled by an operation of a user which operation is part of the dose delivery operation, e.g. by pushing an actuation member. In this way, provision of a efficient and reliable device is facilitated.

According to one embodiment, the dose setting member may comprise a second thread. The second thread may be arranged on an inner surface of the dose setting member. A pitch of the second thread may be less than a pitch of the first thread of the dose setting member. First and second thread may comprise the same thread direction. The assembly further comprises a drive member. The drive member may be arranged at least partly within the dose setting member. The drive member comprises an engagement member, e.g. a threaded portion or a thread. The engagement member may be arranged on an outer surface of the drive member. The engagement member is adapted and arranged to mechanically cooperate with the second thread of the dose setting member. Thus, the dose setting member and the drive member are in threaded engagement. The drive member is prevented from rotation with respect to the housing due to mechanical cooperation with the housing. For example, there is a splined connection between the drive member and the housing.

For setting a dose of the drug, the dose setting member is configured to be rotated in a first direction with respect to the housing and to the drive member, e.g. in a clockwise direction. Upon rotation of the dose setting member, the dose setting member is moved axially with respect to the housing. The dose setting member is moved at least partly out of the housing. In other words, the dose setting member may at least partly unscrew from the housing. Thus, the combined length of housing and dose setting member is increased. When seen with respect to the position of the dose setting member, the housing and the drive member may be shifted, in particular screwed, at least partly out of the dose setting member due to mechanical cooperation of the housing and the drive member with the first and second thread. Upon movement of the dose setting member, the drive member is axially moved in a first direction with respect to the housing from a first position into a second position due to mechanical cooperation of the drive member with the housing and with the dose setting member.

The assembly is configured such that movement of the dose setting member is transferred into movement of the nut member with respect to the piston rod as the dose setting member and the nut member are coupled during dose setting. Movement of the dose setting member may be faster than movement of the nut member. Hence, an axial distance traveled by the nut member with respect to the housing during the dose setting operation may be smaller than the axial distance traveled by the dose setting member with respect to the housing. This may result from a difference of pitches of the first thread of the dose setting member and the thread of the piston rod. The pitch of the thread of the piston rod may be less than the pitch of the first thread of the dose setting member. Accordingly, a minimum axial space is required for the assembly.

According to an embodiment, the displacement distance of the drive member between the first position and the second position is determined by the differences of the pitches of the first and second thread. The pitch of the first thread is preferably greater than the pitch of the second thread. Thus, the displacement distance of the drive member between the first position and the second position may be smaller than the axial distance traveled by the dose setting member with respect to the housing.

According to an embodiment, the assembly is adapted and arranged such that a displacement distance of the nut member with respect to the piston rod during a dose setting operation is less or equal to the displacement distance of the drive member between the first position and the second position during the dose setting operation. Preferably, the displacement distance of the nut member corresponds to the displacement distance of the drive member.

During dose setting, the drive member and the nut member may move independently of one another. In particular, the drive member may be moved due to direct mechanical cooperation, in particular engagement, with the dose setting member. The nut member may be moved due to its coupling with the dose setting member. In other words, during dose setting, movement of the drive member is not transferred into movement of the nut member. Nevertheless, nut member and drive member may move the same distance with respect to the housing due to mechanical cooperation with the dose setting member. The moving distance of the nut member and the drive member may be adjusted to one another. This may be achieved by adjusting the pitches of the second thread of the dose setting member and the thread of the piston rod to one another. The pitches may be equal, for example.

According to an embodiment, the drive member comprises a first face. The first face may be arranged in an end portion of the drive member. The first face may be shaped ring-like. The first face may extend around the end portion of the drive member. The nut member comprises a second face. The second face may be arranged in an end portion of the nut member. The second face may be shaped ring-like. The second face may extend around the end portion of the nut member. The first and the second face may be arranged oppositely to one another. The first face and the second face are adapted and arranged to mechanically cooperate with one another at least during a dose delivery operation. Preferably, the first and the second face are in permanent abutment with one another.

For delivering a set dose of the drug, the dose setting member is configured to be rotated in a second direction with respect to the housing and to the drive member. The second direction may be opposite to the first direction. The second direction may be counter-clockwise. For performing the dose delivery operation, the dose setting member is uncoupled from the nut member. Thus, movement of the dose setting member is no longer directly transferred into movement of the nut member. Hence, the nut member is prevented from rotating during the dose delivery operation.

When seen with respect to the position of the dose setting member, the dose setting member is rotated such that the housing and the drive member are shifted, in particular screwed, at least partly back into the dose setting member. When seen with respect to the housing, upon movement of the dose setting member, the drive member is axially moved in a second direction with respect to the housing from the second position back into the first position. Accordingly, after the delivery operation was completed, the drive member is positioned again in the first position with respect to the housing.

Movement of the drive member is transferred into axial movement of the nut member with respect to the housing due to mechanical cooperation of the first face and the second face. In particular, at least during the dose delivery operation, the first face and the second face are in abutment such that the drive member pushes the nut member in the axial direction. As the nut member mechanically cooperates with the piston rod, in particular as the nut member is in threaded engagement with the piston rod, movement of the nut member is converted into movement of the piston rod with respect to the housing for expelling the set dose out of the cartridge.

A further aspect relates to a drug delivery device. The drug delivery device comprises the previously described assembly. In this way, a very stable and safe device is provided. The device may be especially suited for setting and dispensing small units of drug from the cartridge. For this purpose, parts of the housing, the nut member, the piston rod, the drive member and/or the dose setting member may be especially adapted and arranged for delivering small units, in particular half units. For example, the pitches of the threads of the corresponding components may be adjusted to dispensal of half units of the drug. In particular, the pitches of the threads of the nut member and the piston rod may be reduced as compared to conventional drug delivery devices. The pitch of the second thread of the dose setting member may be increased as compared to conventional drug delivery devices.

The device may be adapted to select a dose of drug in steps of 0.5 units from a minimum of 1 to a maximum of 30 units. Thereby, 1 unit may correspond to 0.01 ml. Hence, a maximum amount of 0.3 ml may be dispensed in one dose delivery operation. Due to the small amounts of drug which can be dispensed from the device, the device may be especially suited for children. If a unit greater than desired was selected, the dose may be turned back down to the desired unit.

Of course, features described above in connection with different aspects and embodiments may be combined with each other and with features described below.

Further features and refinements become apparent from the following description of the exemplary embodiments in connection with the accompanying figures.

Figure 2:
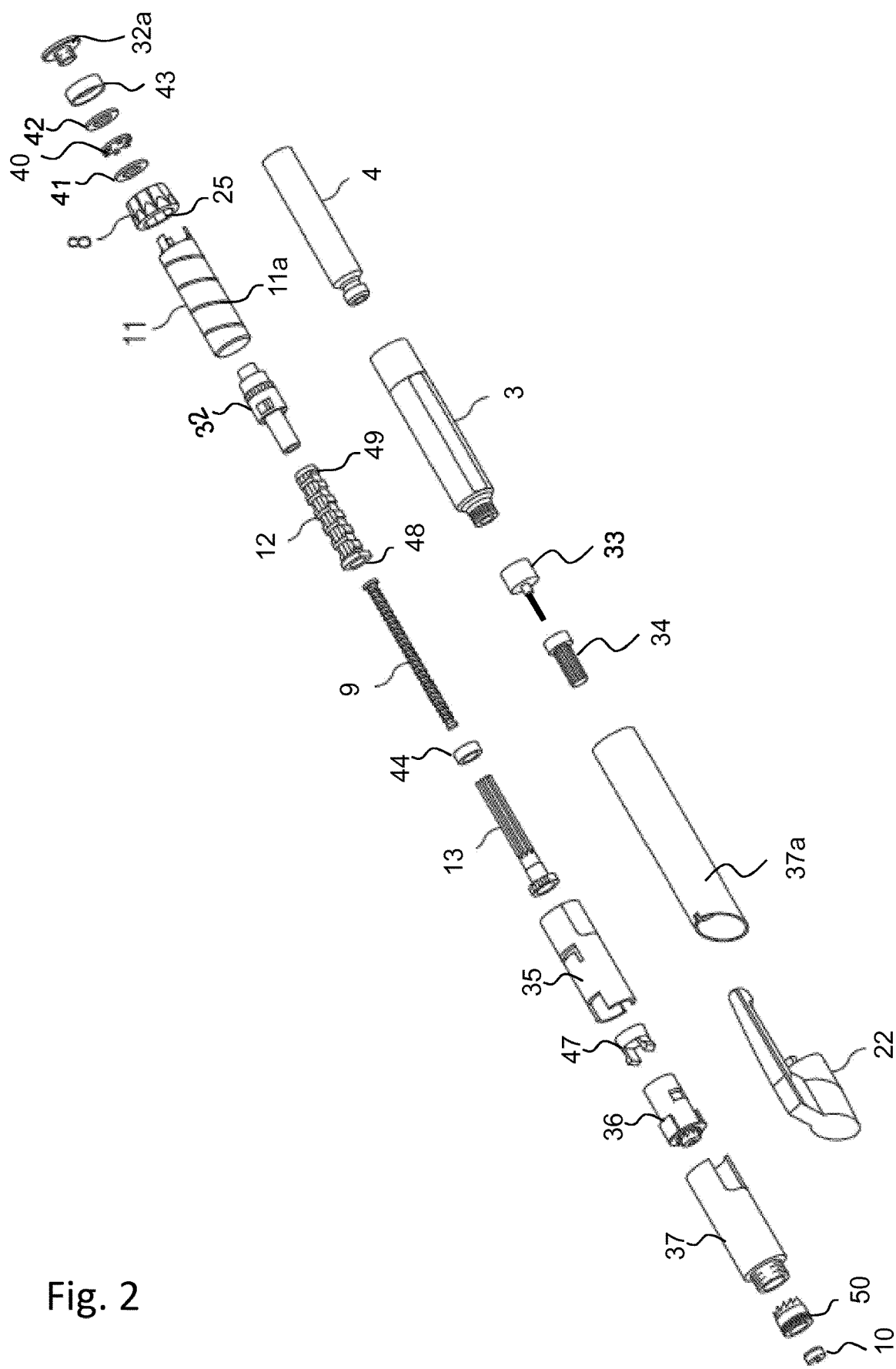
Figure 3A:
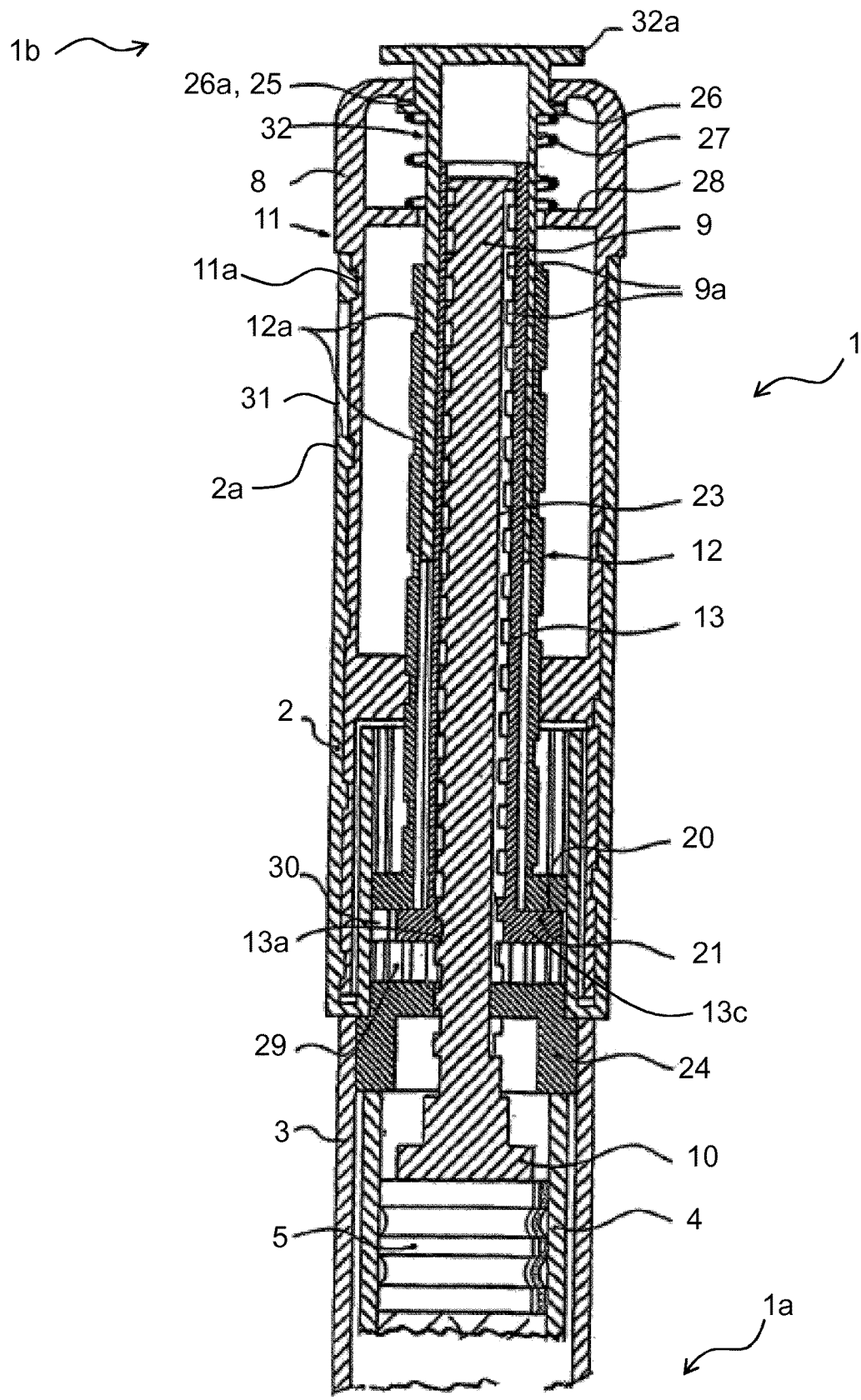
Figure 3B:
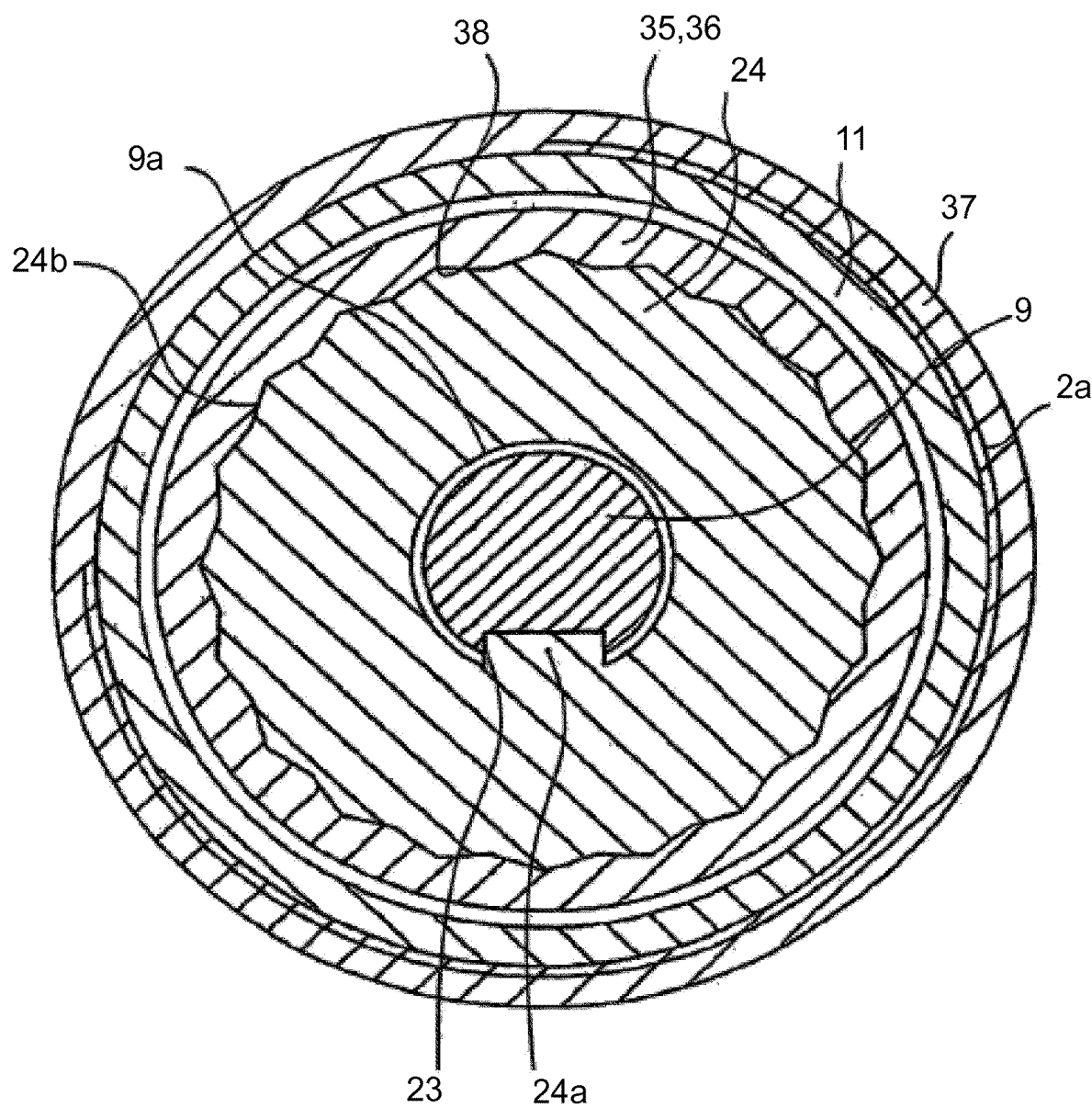
Figure 3C:
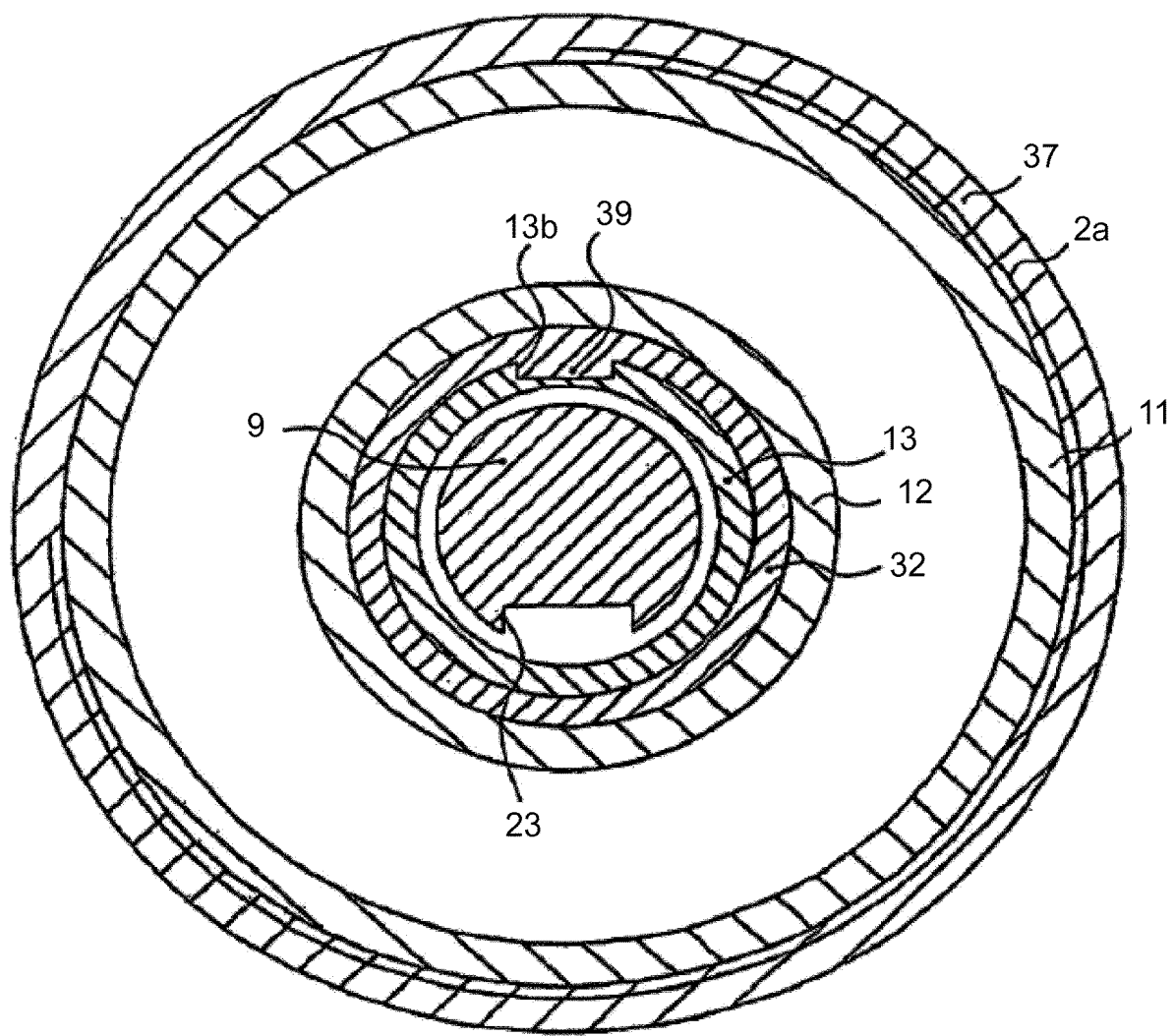
Figure 4:
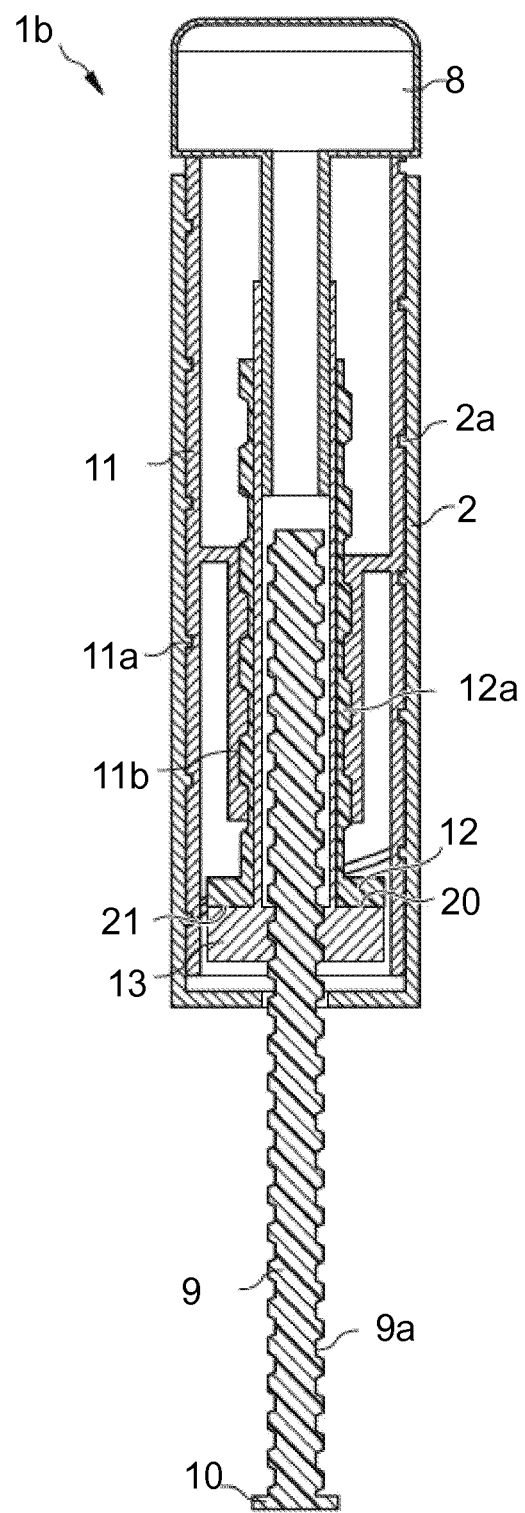
Figure 5A:
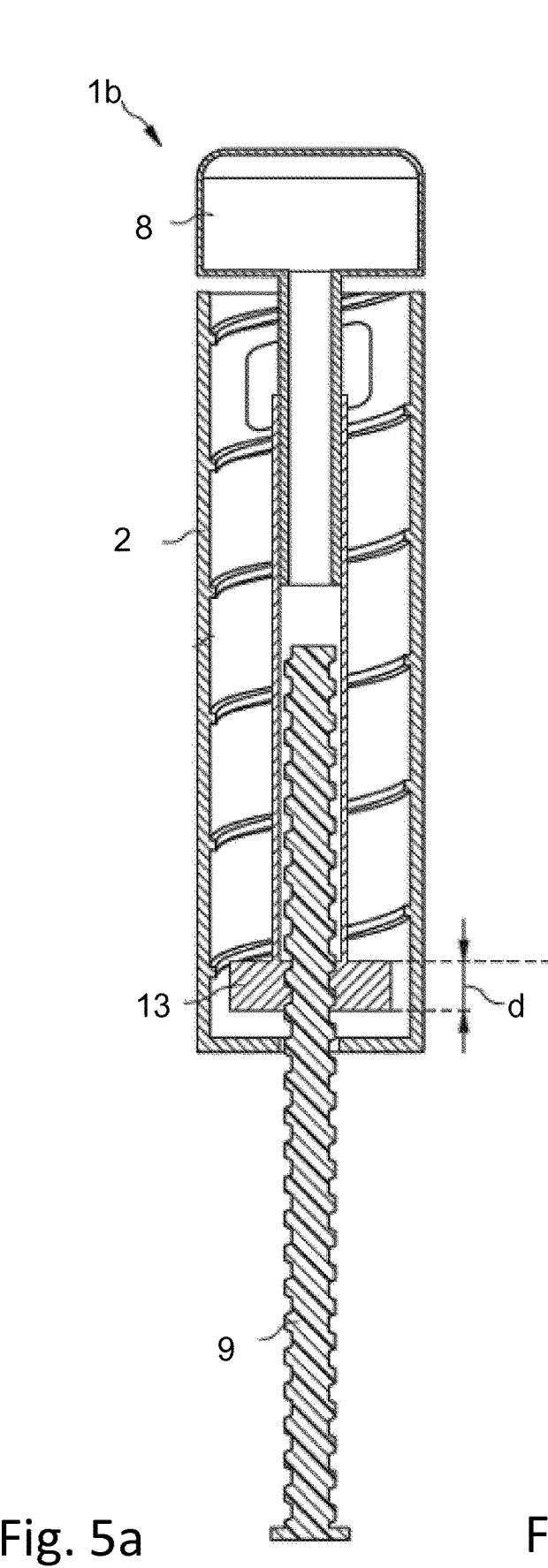
Figure 5B:
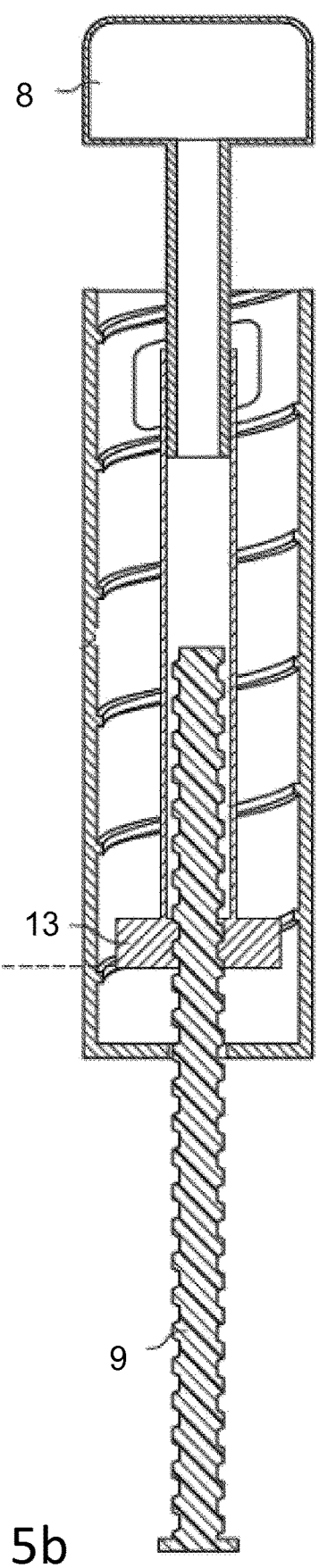
Figure 6A:
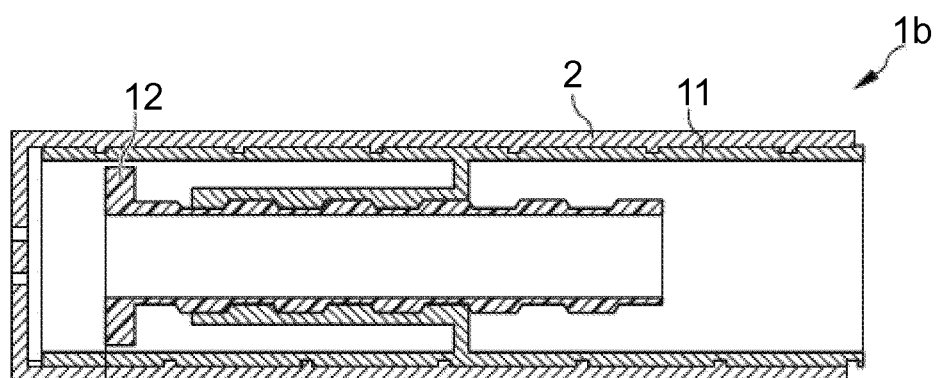
Figure 6B:
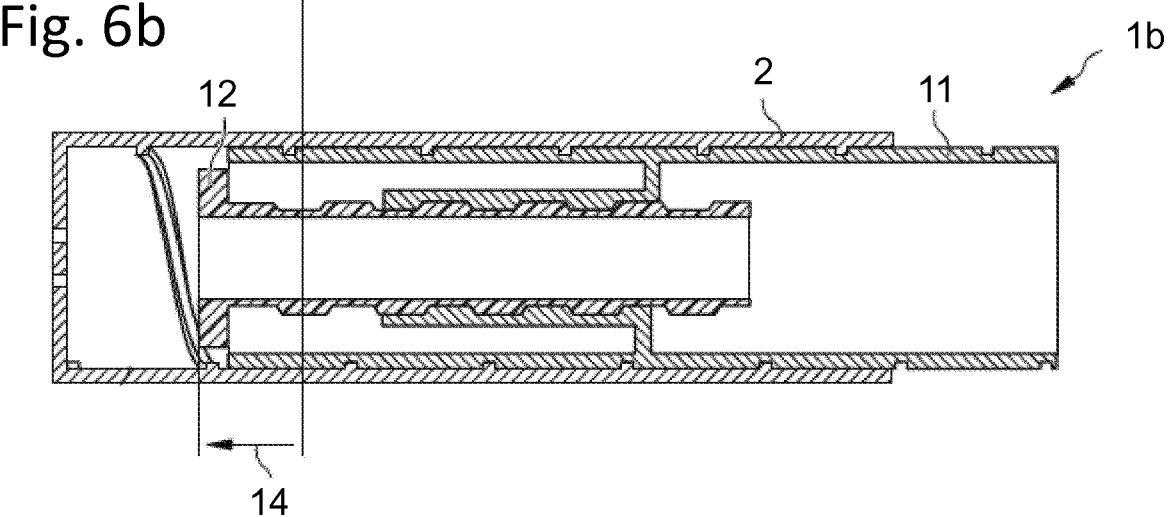
Figure 7A:
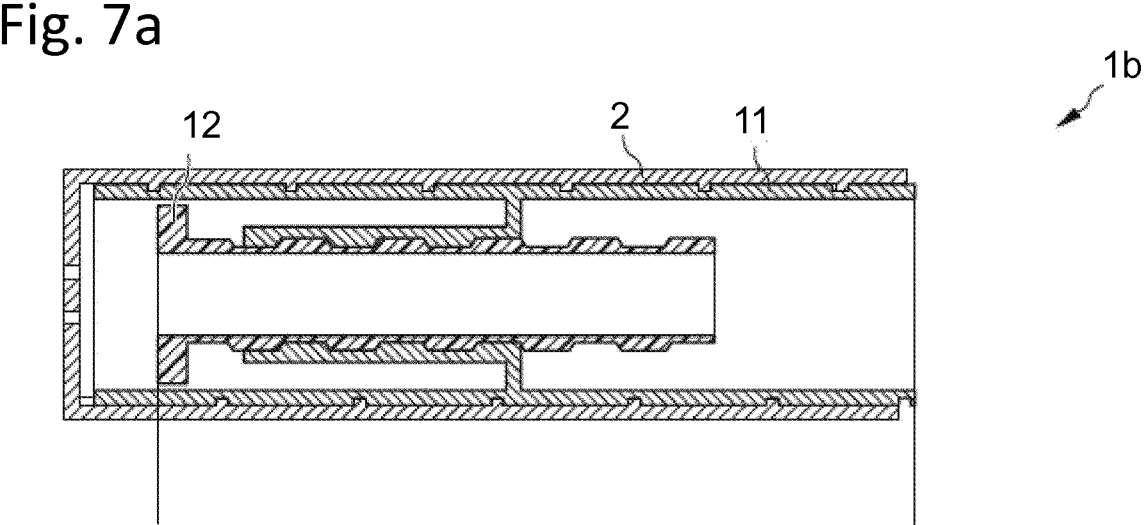
Figure 7B:
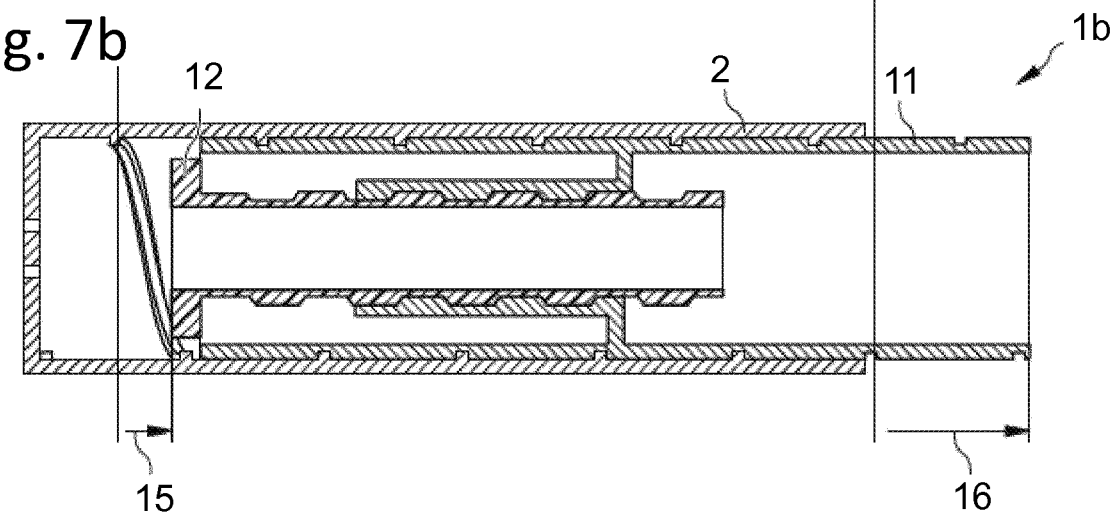
Figure 8:
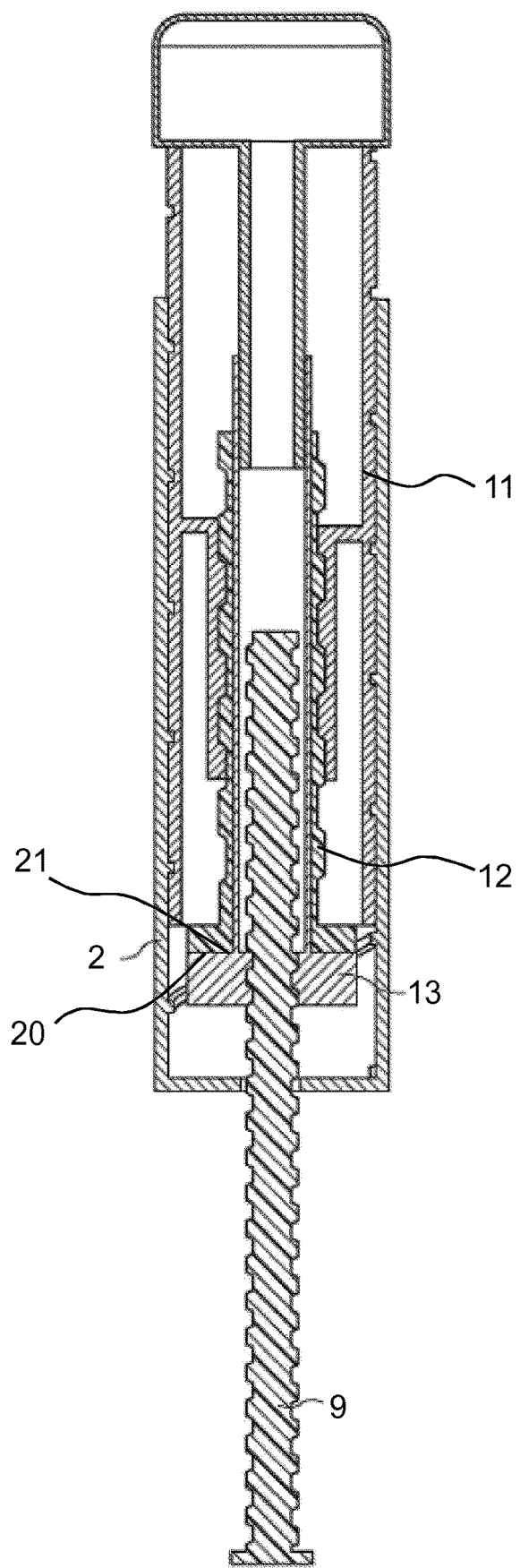
Figure 9:
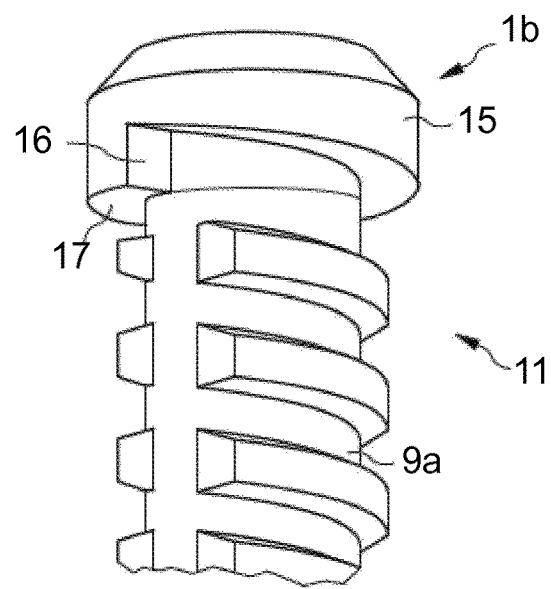
Figure 10:
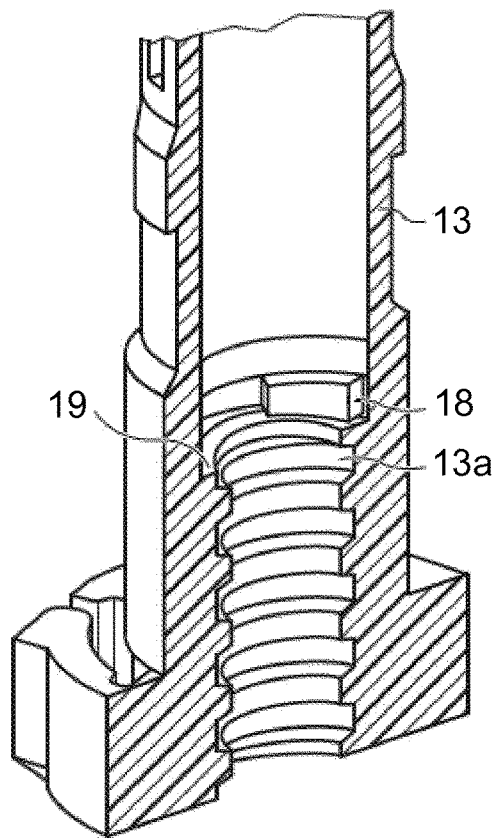
Figure 11A:
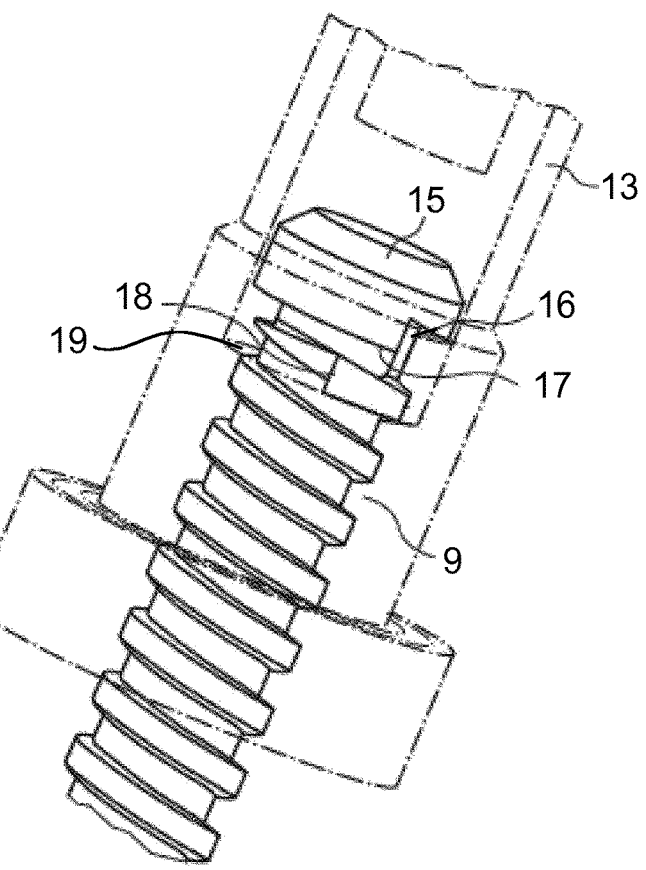
Figure 11B:
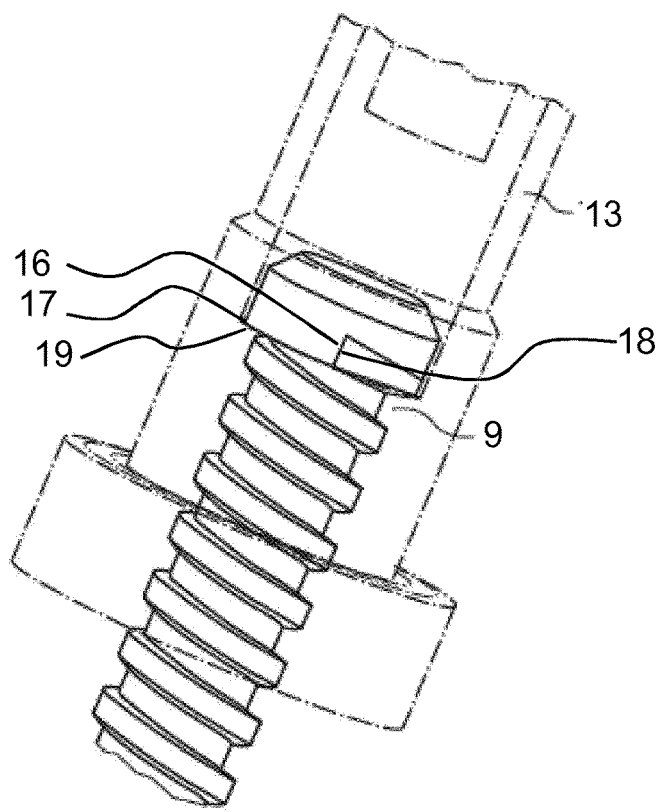
Figure 12:
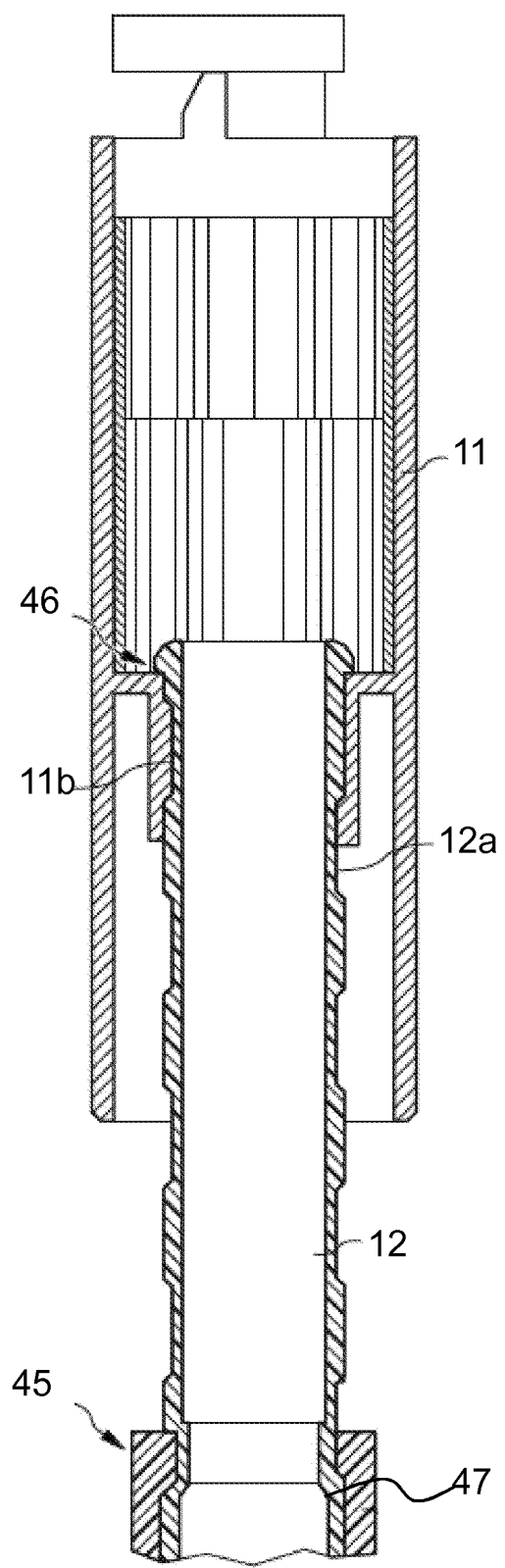

FIGS. 1a and 1b schematically show a sectional side view of a drug delivery device, FIG. 2 shows an exploded view of the drug delivery device of FIGS. 1a and 1b, FIG. 3a shows a sectional side view of parts of the drug delivery device of FIGS. 1a and 1b, FIGS. 3b and 3c show a cross-sectional view of parts of the drug delivery device of FIGS. 1a and 1b, FIG. 4 shows a sectional side view of parts of the drug delivery device of FIGS. 1a and 1b, FIGS. 5a and 5b show a sectional side view of parts of the drug delivery device during a dose setting operation, FIGS. 6a and 6b show a sectional side view of parts of the drug delivery device during a dose setting operation, FIGS. 7a and 7b show a sectional side view of parts of the drug delivery device during a dose setting operation, FIG. 8 shows a sectional side view of parts of the drug delivery device during a dose delivery operation, FIG. 9 shows a sectional side view of a part of the drug delivery device of FIGS. 1a and 1b, FIG. 10 shows a sectional side view of a part of the drug delivery device of FIGS. 1a and 1b, FIGS. 11a and 11b show a sectional side view of parts of the drug delivery device of FIGS. 1a and 1b, FIG. 12 shows a sectional side view of parts of the drug delivery device of FIGS. 1a and 1b.

Like elements, elements of the same kind and identically acting elements may be provided with the same reference numerals in the figures.

In FIGS. 1a, 1b, 2, 3a, 3b and 3c, a drug delivery device 1 is shown. The drug delivery device 1 comprises a housing 2. The housing 2 may comprise a window 31 (see FIG. 3a). The window 31 can serve for displaying dosing information, e.g. a dosing scale. The housing 2 comprises an inner tube 35, 36 and an outer tube 37, 37a (see FIG. 2). An axial dimension of the inner tube 35 and/or 36 is especially adjusted for delivering small units of a drug from the device 1, in particular half units. In particular, the axial dimension is adjusted to house components having specific thread pitches for delivering small units of the drug, e.g. a piston rod 9, a nut member 13, a dose setting member 11 and a drive member 12, which are described later on in detail.

The drug delivery device 1 and the housing 2 have a distal end 1a and a proximal end 1b. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end 1a and the proximal end 1b are spaced apart from one another in the direction of an axis. The axis may be the longitudinal axis or rotational axis 7 of the device 1.

The drug delivery device 1 comprises a cartridge holder 3. The cartridge holder 3 comprises a cartridge 4. The cartridge 4 contains a drug, preferably a plurality of doses of the drug. The cartridge 4 is retained within the cartridge holder 3. The cartridge holder 3 stabilizes the position of the cartridge 4 mechanically. The cartridge holder 3 is connectable, e.g. by a threaded engagement, by a weld or by a snap-fit, to the housing 2. The cartridge holder 3 and the housing 2 may be releasably or irreleasably connected to one another. A bung 5 is slideably retained within the cartridge 4. The bung 5 seals the cartridge 4 proximally. Movement of the bung 5 in the distal direction with respect to the cartridge 4 causes the drug to be dispensed from the cartridge 4.

A needle assembly 33 (see FIG. 2) can be arranged at the distal end of the cartridge holder 3, e.g. by means of a thread 6. A needle cap 34 may be secured to the needle assembly 33 to protect the needle assembly 33 from environmental influences. A cap 22 can be releasably secured to the drug delivery device 1 for protecting the device 1, and, in particular, the cartridge holder 3 or the cartridge 4 from environmental influences, e.g. when the device 1 is not used.

The drug delivery device 1 may be a pen-type device, in particular a pen-type injector. The device 1 may be a re-usable device, which means that the cartridge 4 can be replaced, in particular during a reset operation, by a replacement cartridge for dispensing a plurality of doses from the replacement cartridge. In this case, the cartridge holder 3 may be releasably connected, e.g. threaded, to the housing 2. Alternatively, the device 1 may be a disposable device 1 which means that the cartridge 4 is non replaceable. In this case, the cartridge holder 3 may be non-releasably connected, e.g. glued, to the housing 2.

The drug delivery device 1 comprises a drive mechanism. The drive mechanism comprises in particular a piston rod 9, a drive member 12, a dose setting member 11 and a nut member 13. Furthermore, the drive mechanism comprises a last dose stop mechanism.

The piston rod 9 is arranged within the housing 2 for transferring axial movement to the bung 5 for dispensing a dose of drug from the device 1. For this purpose, the piston rod 9 comprises a bearing member 10 which is arranged in a distal end section of the piston rod 9. The bearing member 10 is shaped disc-like. The bearing member 10 may be a separate component or may be unitarily formed with the piston rod 9. The bearing member 10 may comprise a distal or head portion of the piston rod 9. The bearing member 10 acts onto the bung 5 during a dose delivery operation for moving the bung 5 in the distal direction with respect to the cartridge 4, which is described later on in detail.

The piston rod 9 is moveable in an axial direction with respect to the housing 2. The piston rod 9 is prevented from rotational movement with respect to the housing 2. In particular, the piston rod 9 is not rotatable for setting and dispensing a dose of the drug. The piston rod 9 may be rotatable for resetting the device 1, which is described later on in detail. For preventing rotation of the piston rod 9 during a dose setting and a dose delivery operation, the piston rod 9 comprises a groove 23, as can be seen from FIGS. 3b and 3c. The groove 23 extends along the piston rod 9, in particular along an outer surface of the piston rod 9.

The device 1 may comprise a guiding member 24. The guiding member 24 is axially and rotationally secured to the housing 2, for example by means of a spline set 24b engaging a spline set 38 of the housing 2, in particular of the inner tube of the housing 2 (see FIG. 3b). The guiding member 24 comprises an insert of the housing 2. The guiding member 24 mechanically cooperates with the piston rod 9 for axially guiding the piston rod 9 in the housing 2. The guiding member 24 comprises, for example, a lug or protrusion 24a (see FIG. 3a) for engaging with the groove 23 of the piston rod 9. Mechanical cooperation of the guiding member 24 and the groove 23 prevents the piston rod 9 from rotating with respect to the housing 2. Additionally or alternatively, rotational movement of the piston rod 9 with respect to the housing 2 may be prevented due to mechanical cooperation of the piston rod 9 with a return ring 50 (see FIG. 2). The return ring 50 comprises a toothing. The toothing is arranged in a proximal end section of the return ring 50. When the cartridge 4 is inserted into the device 1, the cartridge 4 pushes the return ring 50 proximally against the force of a spring member (not explicitly shown). Thereby, the return ring 50 is pushed towards a toothing of the inner tube 36 (see FIG. 2). The toothing of the inner tube 36 is arranged in a distal end section of the inner tube 36. Mechanical cooperation of the toothings prevents a rotation of the return ring 50 with respect to the inner tube 36 and, thus, with respect to the housing 2. Due to mechanical cooperation with the return ring 50, rotation of the piston rod 9 may be prevented.

The dose setting member 11 is arranged within the housing 2, in particular within the inner tube of the housing 2. The dose setting member 11 is shaped sleeve-like. At its proximal end, the dose setting member 11 comprises a dose button 8. The dose button 8 and the dose setting member 11 may be formed unitarily. Alternatively, the dose button 8 may be non-moveably connected to the dose setting member 11. The dose button 8 serves a user for setting a dose. The dose button 8 comprises a first clutch member 25, for example a tooth set. The tooth set is arranged on an inner surface of the button 8. The tooth set extends from the button 8 in the axial, in particular distal, direction.

The dose setting member 11 is axially displaceable with respect to the housing 2. The dose setting member 11 is rotatable with respect to the housing 2. The dose setting member 11 comprises a first or outer thread 11a. The first thread 11a is arranged on an outer surface of the dose setting member 11. The housing 2 and, in particular the outer tube, comprises an inner thread 2a (see FIGS. 3a and 3b). The dose setting member 11 is rotatable due to mechanical cooperation of the inner thread 2a and the first thread 11a. On its outer surface, the dose setting member 11 may comprise areas having a dosing scale (not explicitly shown in the Figures) ranging, for example, from "0" to "30," so that the dose setting member 11 can also be called a scale tube. The areas are arranged between windings of the first thread 11a. The areas may be visible through the window 31.

The drive member 12 is arranged within the dose setting member 11. The drive member 12 comprises an engagement member 12a, e.g. a thread or a portion of a thread. The engagement member 12 is arranged on an outer surface of the drive member 12. The engagement member 12 extends along the outer surface of the drive member 12. The dose setting member 11 further comprises a second or inner thread 11b arranged on an inner surface of the dose setting member 11 for mechanically cooperating with the engagement member 12a. Due to mechanical cooperation of engagement member 12 and inner thread 11b, the dose setting member 11 is rotatable and axially displaceable with respect to the drive member 12 for setting and delivering a dose of the drug. The pitch of the thread 11b may be adapted for dispensing a small amount of drug from the cartridge 4, e.g. a half-unit. Thus, the pitch may be greater as compared to the pitch of a dose setting member of a conventional device.

The drive member 12 is prevented from rotational movement with respect to the housing 2. The drive member 12 is in splined connection with the housing 2, in particular with the inner tube of the housing 2. For this purpose, the drive member 12 comprises a lug or protrusion on its outer surface (not explicitly shown in the Figures) and the housing 2, in particular the inner tube of the housing 2, comprises the previously mentioned spline set 38 on its inner surface. Mechanical cooperation of the spline set 38 and the drive member 12 leads to an axial guidance of the drive member 12 within the housing 2, thereby preventing rotational movement of the drive member 12 with respect to the housing 2.

During a dose setting operation, the drive member 12 is axially, in particular proximally, displaceable with respect to the housing 2 from a start position to an end position. The start position is that position the drive member 12 is arranged in when the device 1 is supplied from the manufacturer. The end position is a pre-delivery position, i.e. a position the drive member 12 is arranged in before the set dose is delivered. The end position may depend of the amount of the set dose. Hence, a distance the drive member 12 travels during the setting operation corresponds to the amount of drug which is set. During the delivery operation, the drive member 12 is axially, in particular distally, displaceable with respect to the housing 2 from the end position back to the start position. Hence, after delivery of the set dose, the drive member 12 has the same position with respect to the housing 2 as before setting the respective dose.

The nut member 13 is arranged at least partly within the drive member 12. The nut member 13 is arranged at least partly around the piston rod 9. The nut member 13 may comprise a circular nut or a ratchet member. The nut member 13 is shaped sleeve-like. The nut member 13 comprises a distal portion 13c. The distal portion 13c comprises a greater diameter than a remaining part of the nut member 13. The distal portion 13c is shaped ring-like. The distal portion 13c may be formed unitarily with the remaining part of the nut member 13 or may be connected to the remaining part. The distal portion 13c comprises a second or proximal face 21. The drive member 12 comprises a head or distal portion. The head portion comprises a first or distal face 20. During operation, i.e. during dose setting and dose delivery, of the device 1, distal face 20 and proximal face 21 are in abutment, preferably in permanent abutment.

The nut member 13 comprises an inner thread 13a. The piston rod 9 comprises a thread 9a arranged on the outer surface of the piston rod 9. The thread 9a extends along the outer surface of the piston rod 9. The pitch of the thread 9a may be greater than 1 mm and smaller than 2 mm. The pitch of the thread 9a may be 1.3 mm or 1.4 mm, for example 1.395 mm. The pitch of the threads 9a, 13a may be adapted for dispensing a small amount of drug from the cartridge 4, e.g. a half-unit. Thus, the pitch may be smaller as compared to the pitch of a piston rod and a nut member of a conventional device. The nut member 13 is engaged, preferably permanently engaged, with the piston rod 9 due to mechanical cooperation of the threads 9a, 13a. A supporting ring 44 (see FIG. 2) is provided for supporting the stability of the nut member 13 in the region of the inner thread 13.

The distal portion 13c of the nut member 13 further comprises a snap feature 30 (see FIG. 3a). The snap feature 30 extends from the distal portion 13c in the radial direction. The snap feature 30 may be attached to the distal portion of the nut member 13 or may be formed integrally with the distal portion 13c. The snap feature 30 may comprise a resilient tongue, for example. The snap feature 30 rests with preload against a spline set 29 of the housing 2 (see FIG. 3a). During a dose delivery operation, the snap feature 30 is displaced axially in the spline set 29 such that the nut member 13 is moveable in the distal direction with respect to the housing 2 during dose delivery. However, during dose delivery, the nut member 13 is not rotatable, which is explained later on in detail.

Although being in splined engagement with the housing 2, the nut member 13 is rotatable with respect to the housing 2 during a dose setting operation. During a dose setting operation, the nut member 13 is rotatable with respect to the piston rod 9 and with respect to the housing 2 due to mechanical cooperation with the dose setting member 11. The nut member 13 may be arranged in 20 different radial positions with respect to the housing 2. During rotation, the interaction of the snap feature 30 and the spline set 29 creates a clicking sound. In this way, the user can hear and feel a plurality of clicks for each revolution of the dose setting member 11. Thus, the user may also set the dose by ear or by feel, since an audible and perceptible signal is generated for each dose increment. In addition, a set dose cannot unintentionally be changed, since a predetermined minimum torque is necessary for any adjustment in either rotation direction.

When the nut member 13 is rotated during dose setting, it is axially displaced along the piston rod 9 from a start position towards an end position with respect to the piston rod 9, which is explained later on in detail. When the nut member 13 is positioned in the end position, the last dose of drug has already been dispensed from the cartridge 4. This is explained in connection with the last dose stop mechanism.

During dose setting, the nut member 13 is secured against rotation with respect to the dose setting member 11. In other words, the nut member 13 is rotationally coupled to the dose setting member 11. For this purpose, the nut member 13 comprises a groove 13b (see FIG. 3c). The groove 13b is arranged on an outer surface of the nut member 13. The groove 13b extends along the outer surface of the nut member 13b. The device 1 further comprises a entrainment means 32. The entrainment means 32 rotationally couples the dose setting member 11 and the nut member 13 during dose setting. The entrainment means 32 is configured to rotationally decouple the dose setting member 11 and the nut member 13 during dose delivery.

The entrainment means 32 is arranged within the dose setting member 11 and the drive member 12. It extends through the button 8, in particular it projects from the proximal end of the button 8. The entrainment means 32 comprises a radial protrusion 39 (see FIG. 3b). The protrusion 39 engages with the groove 13b of the nut member 13. The entrainment means 32 is slidably arranged on the outer surface of the nut member 13 such that the protrusion 39 slides in the groove 13b, thereby non-rotatably coupling the nut member 13 and the entrainment means 32 to one another.

The entrainment means 32 comprises an actuation member 32a. The actuation member 32a is arranged in a proximal end section of the entrainment means 32 (see FIG. 3a). The actuation member 32a may comprise an actuation plate the user may push in the distal direction for delivering the set dose. The actuation member 32a is placed within a ring member 43 which is arranged in the interior of the button 8. The actuation member 32a extends from the button 8 in a proximal direction.

The entrainment means 32 comprises a flange 26. The flange 26 comprises a second clutch member 26a, e.g. a tooth set. The tooth set 26a is arranged on a proximal side of the flange 26. In particular, the tooth set extends from the flange 26 in the proximal direction. The tooth set 26a mechanically cooperates with the tooth set 25 of the button 8 to form a clutch mechanism 25, 26a. The tooth sets are configured to releasably engage with one another. When the tooth sets are engaged with one another during dose setting, the entrainment means 32 and the dose setting member 11 are coupled with one another such that relative rotation between the entrainment means 32 and the dose setting member 11 is prevented. Accordingly, when the tooth sets are engaged with one another, the dose setting member 11 and the nut member 13 are rotationally locked with one another via the entrainment means 32.

The device 1 further comprises a spring 27, in particular a compression spring 27. The spring 27 exerts an axial, in particular proximal, force onto the flange 26. The spring 27 is arranged between the flange 26 and a support flange 28 of the dose setting member 11. The spring 27 acts onto the flange 26 such that the tooth sets 25, 26a are engaged with one another as long as the user does push onto the actuation member 32a. Thus, during a dose setting operation, the tooth sets are engaged. When the user pushes onto the actuation member 32a for delivering a set dose, the spring 27 is compressed and the tooth sets 25, 26a are brought out of engagement, thereby decoupling the entrainment means 32 and the dose setting member 11 and, thus, decoupling the dose setting member 11 and the nut member 13 during the dose delivery operation. Thus, during the dose delivery operation, the nut member 13 is not rotatable with respect to the piston rod 9 as it is no longer coupled to the dose setting member 11.

The drive mechanism further comprises the previously mentioned last dose stop mechanism (see, in particular, FIGS. 9, 10, 11a and 11b). This mechanism prevents the user from setting a dose of the drug which exceeds a remaining amount of drug in the cartridge 4. The last dose stop mechanism comprises a first and a second stop member 18, 19. Alternatively, the mechanism may comprise two, three or more first stop members 18 and/or two, three or more second stop members 19. The stop members 18, 19 are provided by the nut member 13. The stop members 18, 19 are arranged in a distal end section of the nut member 13. The stop members 18, 19 are arranged on an inner surface of the nut member 13 (see FIG. 10). The stop members 18, 19 may be part of the inner thread 13a. The first stop member 18 comprises a radial stop face. This means that the first stop member 18 protrudes from the inner surface of the nut member 13 in a radial direction, in particular radially inwardly. The second stop member 19 comprises an axial stop face. The second stop member 19 protrudes in an axial, in particular proximal, direction from the nut member 13.

The last dose stop mechanism further comprises a first and a second interaction member 16, 17. Alternatively, the mechanism may comprise two, three or more first interaction members 16 and/or two, three or more second interaction members 17. The interaction members 16, 17 are provided by the piston rod 9, in particular by a proximal end section of the piston rod 9. The interaction members 16, 17 are arranged on the outer surface of the proximal end section of the piston rod 9. The first interaction member 16 comprises a radial stop face. This means that the first interaction member 16 protrudes from the piston rod 9 in a radial direction. A radial dimension or width of the first interaction member 16 may be smaller than 0.5 mm. The radial dimension is preferably smaller than 0.45 mm, for example it amounts to 0.43 mm or less. Preferably, the radial dimension is 0.40 mm. An axial dimension or height of the first interaction member 17 may be smaller than 1.4 mm. The axial dimension is preferably 1.395 mm, 1.39 mm or 1.385 mm. The axial dimension may be equal to the pitch of the thread 9a.

The second interaction member 17 comprises an axial stop face. The proximal end section of the piston rod 9 has a diameter which is greater than the outer diameter of the remaining parts of the piston rod 9. In other words, the proximal end section projects from the surface of the piston rod 9. The second interaction member 17 extends from the proximal end section in distal direction. In other words, it comprises at least partly the distal face of that projection or proximal end section of the piston rod 9. The first interaction member 16 comprises a radial face of that projection or proximal end section.

When the nut member 13 is in the end position with respect to the piston rod 9, the interaction members 16, 17 mechanically cooperate with the stop members 18, 19 such that further relative movement of the nut member 13 and the piston rod 9 for setting a dose of the drug is prevented. Thus, a further dose setting operation is prevented. However, the nut member 13 may be enabled to travel back towards the start position, e.g. for a dose correction operation of the device 1.

The first interaction member 16 mechanically cooperates with the first stop member 18 to form a radial end stop. Mechanical cooperation of the first interaction member 16 and the first stop member 18 prevents the nut member 13 from further rotation with respect to the piston rod 9 for setting a further dose. The second interaction member 17 mechanically cooperates with the second stop member 19 to form an axial end stop. Mechanical cooperation of the second interaction member 17 and the second stop member 19 prevents the nut member 13 from further axial, in particular proximal, movement with respect to the piston rod 9 for setting a further dose. Thus, the last dose stop mechanism provides two stop mechanisms, i.e. an axial and a radial mechanism which work on parallel. In particular, the relative rotation of nut member 13 and piston rod 9 during a dose setting operation is stopped by the radial end stop in the same position, i.e. the end position, in which the relative axial movement of the nut member 13 and the piston rod 9 during a dose setting operation is stopped by the axial end stop. A distance between the first interaction member 16 and the first stop member 18 during the operation of the device 1 corresponds to the remaining amount of drug in the cartridge 4. The same applies for the distance between the second interaction member 17 and the second stop member 19.

Mechanical cooperation of the stop members 18, 19 and the interaction members 16, 17 determines the end position of the nut member 13 with respect to the piston rod 9. The length of the axial travel of the nut member 13 on the piston rod 9 corresponds to the maximum number of doses of the drug which can be dispensed from the device 1. For instance, when the cartridge 4 contains 300 units of the drug in maximum, the whole number of units is still in the cartridge 4, when the nut member 13 is positioned in the start position. The nut member 13 is in the end position when no additional units of the drug are available. When the nut member 13 is arranged approximately half-way between the start position and the end position with respect to the piston rod 9, about 150 units of the drug are still available in the cartridge 4.

In the following, operation of the device for setting and dispensing a dose of the drug is described in connection with the FIGS. 4 to 11b.

In FIG. 4, the device 1 is shown before setting a dose of the drug. The drive member 12 is arranged in the previously described start position with respect to the housing 2. The distal face 20 of the drive member 12 abuts the proximal face 21 of the nut member 13. The nut member 13 is rotationally coupled to the dose setting member 11 by means of the clutch mechanism 25, 26a as described above.

FIGS. 5a and 5b illustrate the movement of the button 8 and nut member 13 during the dose setting operation. As mentioned above, the button 8 is part of the dose setting member 11. However, for clarity reasons, FIGS. 5a and 5b show only the button 8 of the dose setting member 11. For setting the dose, the user screws the button 8 and, thus, the dose setting member 11 out of the housing 2 (see FIG. 5b). Hence, the button 8 is rotated and moved proximally. The button 8 may rotate clockwise, for example. As the nut member 13 is rotationally coupled to the dose setting member 11 by means of the entrainment means 32, the nut member 13 rotates with respect to the piston rod 9 and travels in the proximal direction towards the end position. Accordingly, during dose setting, the movement of the dose setting member 11 is directly transferred into movement of the nut member 13 by means of the entrainment means 32. The nut member 13 and the dose setting member 11 rotate in the same direction, e.g. clockwise.

The dose setting member 11 moves faster proximally than the nut member 13. The dose setting member 11 moves 10 mm per revolution, for example. The nut member 13 moves more than or equal to 1.395 mm per revolution. The nut member 13 moves less than 2 mm per revolution, for example 1.5 mm, 1.45 mm or 1.4 mm per revolution. Hence, a distance d the nut member 13 travels proximally with respect to the housing 2 during dose setting is smaller than a distance the button 8 and, thus, the dose setting member 11 moves proximally. The difference in the distances may be determined by the difference in the pitches of the threads 9a, 13a and 2a, 11a. The pitch of the threads 9a, 13a is smaller than the pitch of the threads 2a, 11a, which can be seen from FIG. 4, for example. When the dose setting operation is completed, the nut member 13 is arranged closer to the end position with respect to the piston rod 9 than before the respective dose setting operation has taken place.

FIGS. 6a and 6b illustrate the movement of the drive member 12 and the housing 2 with respect to the dose setting member 11 during the dose setting operation. As described above, the button 8 and, thus, the dose delivery member 11 is rotated for setting a dose of the drug. The housing 2 and the drive member 12 are not rotatable. Accordingly, during dose setting, the drive member 12 and the housing 2 unscrew from the dose setting member 11 as indicated by arrow 14 in FIG. 6b.

FIGS. 7a and 7b illustrate the movement of the drive member 12 and the dose setting member 11 with respect to the housing 2 during the dose setting operation. As the dose setting member 11 rotationally moves in the proximal direction (see arrow 16 in FIG. 7b) with respect to the housing 2, the drive member 12 is moved proximally with respect to the housing 2 (see arrow 15 in FIG. 7b) due to mechanical cooperation with the second thread 11b. The drive member 12 is moved from the first position (FIG. 7a) into the second position (FIG. 7b). Thereby, the distance by which the drive member 12 is moved proximally is smaller than the distance by which the dose setting member 11 is moved proximally. The displacement distance of the drive member 12 between the first position and the second position is determined by the differences of the pitches of threads 11a, 2a and threads 11b, 12a. In particular, the pitch of threads 11b, 12a is smaller than the pitch of threads 11a, 2a, as can be seen from FIGS. 7a and 7b.

The displacement distance d of the nut member 13 with respect to the piston rod 9 and to the housing 2 during the dose setting operation may be less or equal to the displacement distance of the drive member 12 between the first position and the second position. In this embodiment, the displacement distances are equal, as can be seen from FIGS. 7b (arrow 15) and 5b (distance d). Thus, although the drive member 12 and the nut member 13 move independently from one another during dose setting, i.e. are not coupled, they move the same distance. For this purpose, the pitch of the threads 9a, 13a may be equal to the pitch of the threads 11b, 12a. During movement of the drive member 12, the faces 20, 21 remain in abutment.

If, in an alternative embodiment, the drive member 12 is designed to move more than the nut member 13, the drive member 12 pulls the nut member 13 and, thus, the piston rod 9 in proximal direction during the dose setting operation. In this way, interaction of the piston rod 9 and the bung 5 during dose setting may be prevented and, thus, dose accuracy may be increased.

After completion of the dose setting operation, nut member 13 and drive member 12 have moved proximally for the same distance and the dose setting member 11 has moved further in the proximal direction than the nut member 13 and the drive member 12. The piston rod 9 is prevented from movement during the dose setting operation due to mechanical cooperation with the housing 2.

If the dose selected was too high, i.e. if the dose setting member 11 was moved too far in the proximal direction, the user may rotate the dose button 8 and, thus, the dose setting member 11 in an opposite direction, e.g. counter-clockwise, for correcting the set dose to a smaller value. Thereby, the drive member 12 is moved distally. The nut member 13 is also moved distally for the same distance as the drive member 12 and—as the nut member 13 is still coupled to the dose setting member 11—the nut member 13 is rotated in the opposite direction, e.g. counter-clockwise—with respect to the piston rod 9.

The device 1 further comprises a maximum dose end stop to limit the maximum settable dose to 30 units. The maximum dose end stop comprises two axial end stops 45, 46. The axial end stops 45, 46 may be arranged more distally as compared to axial end stops of conventional drug delivery devices. The first end stop 46 is implemented between the drive member 12 and the dose setting member 11. The drive member 12 comprises a first interface member 49 (see FIG. 2). The first interface member 49 may comprise a protrusion. The first interface member 49 protrudes from the drive member 12 in a radial direction. The first interface member 49 is arranged in a proximal end section of the drive member 12. The first interface member 49 may be part of the thread 12a. The dose setting member 11 comprises a corresponding first interface member. The interface member protrudes from the dose setting member 11 radially inwardly. The first interface member may be part of the second thread 11b of the dose setting member 11. The first interface member of the dose setting member 11 may be a flange being arranged circumferentially on the inner surface of the dose setting member 11. The first interface member of the dose setting member 11 may be arranged in a proximal end section of the dose setting member 11. After three complete rotations of the dose setting member 11, corresponding to a set dose of 30 units, the first interface members of drive member 12 and dose setting member 11 abut such that further displacement of the drive member 12 in the proximal direction is prevented.

The second end stop 45 is implemented between the drive member 12 and a snap ring 47. The snap ring 47 is snapped to the inner tube front 36 (see FIG. 2). The axial dimension of the inner tube 36 is specifically adjusted for snapping the snap ring 47 to the inner tube 36. In particular, the axial dimension may be chosen such that the snap ring 47 comprises a position which is more distally with respect to the housing 2 than a position of a snap ring of conventional devices. The axial dimension is chosen such that an axial position of the snap ring 47 is adjusted to the specific thread pitches of the device 1, for example to the pitches of threads 9a, 13a, 12a and 11b. By means of snapping the snap ring 47 to the inner tube 36, the snap ring 47 is secured against axial and rotational movement with respect to the housing 2. The drive member 12 comprises a second interface member 48 (see FIG. 2). The second interface member 48 may comprise a protrusion. The second interface member 48 protrudes from the drive member in a radial direction. The second interface member 49 is arranged in a distal end section of the drive member 12. The second interface member 48 may be part of the thread 12a. After three complete rotations of the dose setting member 11, corresponding to a set dose of 30 units, the second interface member 48 engages with the snap ring 47 such that further displacement of the drive member 12 in the proximal direction is prevented.

For injecting the set dose, the user pushes onto the actuation member 32a. To ensure a smooth injection, a ball bearing 40, 41, 42 is implemented between the rotating parts (dose setting member 11, button 8) and the non-rotating parts (actuation member 32a, ring 43), as can be seen in FIG. 2. When the actuation member 32a is pushed distally, the nut member 13 and the dose setting member 11 are decoupled from one another, as described above. Consequently, rotational movement of the dose setting member 11 is no longer transferred into rotational movement of the nut member 13. By means of the distal force exerted onto the actuation member 32a, the dose setting member 11 is screwed back in the distal direction since it has a coarse thread that automatically executes a screwing motion under axial pressure. Rotation of the dose setting member 11 may be amplified by the torque of a torsional spring (not explicitly shown in the Figures). Said torsional spring may be arranged between the dose setting member 11 and the drive member 12. A distal end of the torsional spring may be non-rotatably connected to the dose setting member 11. A proximal end of the torsional spring may be non-rotatably connected to the distal end of the drive member 12.

As the dose setting member 11 moves in the distal direction, the drive member 12 is moved distally back to the first position due to mechanical cooperation with the second thread 11b. Thereby, the faces 20, 21 mechanically cooperate with one another such that the drive member 12 pushes the nut member 13 and, thus, the piston rod 9, in the distal direction. Accordingly, during dose delivery, movement of the dose setting member 11 is only indirectly transferred into movement of the nut member 13 by means of the drive member 12. The piston rod 9 moves the bung 5 distally for expelling the dose. During injection, the bung 5 moves the equal distance as the piston rod 9.

After the dose delivery operation was completed, the dose setting member 11 and the drive member 12 have substantially the same position with respect to the housing 2 as before the delivered dose was set. After the dose delivery operation was completed, the nut member 13 is arranged closer to the end position with respect to the piston rod 9 than before the delivered dose was set.

After a plurality of dose setting and dose delivery operations, the cartridge 4 may be emptied or the remaining amount of drug in the cartridge 4 may be less than a dose to be set. In order to prevent that the user sets a dose of the drug which exceeds a remaining amount of drug in the cartridge 4, the device 1 comprises the previously described last dose stop mechanism. FIG. 11a shows the piston rod 9 in a position of 330° before the stop members 18, 19 and the interaction members 16, 17 get into abutment. When the user tries to set a further dose, the nut member 13 screws proximally with respect to the piston rod 9 until the first interaction member 16 mechanically cooperates with the first stop member 18 (radial end stop) and the second interaction member 17 mechanically cooperates with the second stop member 19 (axial end stop) as shown in FIG. 11a. Once the stop members 18, 19 are in engagement with the interaction members 16, 17, movement of the nut member 13 with respect to the piston rod 9 is no longer possible. In other words, a further dose setting operation is not possible.

Now, the cartridge holder 3 may be disconnected from the housing 2 in order to replace the cartridge 4 by a replacement cartridge during a reset operation. During reset, the piston rod 9 is screwed axially, in particular proximally, into the housing 2 until it is arranged in the same position as supplied from the manufacturer. This may be an initial position of the piston rod 9. When moving the piston rod 9 into the initial position, the user must hold the return ring 50 (see FIG. 2). By means of the return ring 50 rotation of the piston rod 9 with respect to the housing 2 is prevented when setting and dispensing a dose of the drug, as described above. When the cartridge holder 3 and, thus, the cartridge 4 was removed, the spring member (not explicitly shown) pushes the return ring 50 distally as the cartridge 4 no longer exerts a proximal force onto the return ring 50. Thus, when the cartridge 4 is removed, the toothed connection between the return ring 50 and the inner tube 36 is dissolved. Hence, during reset, the return ring 50 is rotatable with respect to the housing 2. When the user rotates the return ring 50 with respect to the housing 2, the piston rod 9 is rotated with respect to the housing 2 and with respect to the nut member 13 due to mechanical cooperation with the return ring 50. In this way, the piston rod 9 is rotatable and moveable proximally towards the initial position. The nut member 13 is not moved when resetting the device 1.

When the piston rod 9 is positioned in the initial position, the cartridge holder 3 comprising the replacement cartridge is connected to the housing 2. In a priming step, the bearing member 10 must be brought into contact with the bung 5. For this purpose, the piston rod 9 is moved distally until it gets in contact with the bung 5. Afterwards, the device 1 is ready for dispensing a plurality of doses from the replacement cartridge.

Other implementations are within the scope of the following claims. Elements of different implementations may be combined to form implementations not specifically described herein.

REFERENCE NUMERALS

1 Drug delivery device
1a Distal end
1b Proximal end
2 Housing
2a Inner thread
3 Cartridge holder
4 Cartridge
5 Bung
6 Thread
7 Rotational axis
8 Button
9 Piston rod
9a Thread
10 Bearing member
11 Dose setting member
11a First thread
11b Second thread
12 Drive member
12a Engagement member
13 Nut member
13a Thread
13b Groove
13c Distal portion
d Distance
14 Arrow
15 Arrow
16 First interaction member
17 Second interaction member
18 First stop member
19 Second stop member
20 First face
21 Second face
22 Cap
23 Groove
24 Guiding member
24a Protrusion
24b Spline set
25 First clutch member
26 Flange
26a Second clutch member
27 Spring
28 Flange
29 Spline set
30 Snap feature
31 Window
32 Entrainment means
32a Actuation member
33 Needle
34 Needle cap
35 Inner Tube rear
36 Inner tube front
37, 37a Outer tube of the housing
38 Spline set
39 Protrusion
40, 41, 42 Ball bearing
43 Ring member
44 Supporting ring
45 End stop maximum dose
46 End stop maximum dose
47 Snap ring
48 Second interface member
49 First interface member
50 Return ring

The invention claimed is:

1. An assembly for a drug delivery device, the assembly comprising:
a cartridge containing a plurality of doses of a drug;
a piston rod configured to be arranged within a housing of the drug delivery device, the piston rod adapted and arranged to transfer axial movement of the piston rod to a bung of the cartridge for expelling the drug from the cartridge during a dose delivery operation of the assembly, the piston rod comprising a thread;
a nut member, wherein the nut member is adapted and arranged to be rotated with respect to the piston rod about a rotational axis during a dose setting operation of the assembly, the nut member thereby being axially displaced along the piston rod from a start position towards an end position with respect to the piston rod due to mechanical cooperation of the nut member with the thread of the piston rod; and
a last dose stop mechanism adapted and arranged to prevent a user from setting a dose of the plurality of doses of the drug which exceeds a remaining amount of the drug in the cartridge, the last dose stop mechanism comprising at least one first interaction member and at least one second interaction member provided by the piston rod and at least one first stop member and at least one second stop member provided by the nut member,
wherein the at least one first stop member protrudes radially inwardly from an inner surface of the nut member, and
wherein the at least one first and second interaction members and the at least one first and second stop members are configured to mechanically cooperate with one another when the nut member is in the end position with respect to the piston rod such that further relative movement of the nut member and the piston rod for dose setting is prevented.

2. The assembly according to claim 1, wherein the last dose stop mechanism comprises a radial end stop, wherein the at least one first stop member and the at least one first interaction member each comprise at least one radial stop face, wherein the radial stop faces are configured to mechanically cooperate with one another when the nut member is in the end position with respect to the piston rod such that further rotation of the nut member with respect to the piston rod for setting a dose of drug is prevented.

3. The assembly according to claim 1, wherein the last dose stop mechanism comprises an axial end stop, wherein the at least one second stop member and the at least one second interaction member each comprise at least one axial stop face, wherein the axial stop faces are configured to mechanically cooperate with one another when the nut member is in the end position with respect to the piston rod such that further axial movement of the nut member with respect to the piston rod for dose setting is prevented.

4. The assembly according to claim 1, wherein the assembly is configured such that a distance between the at least one first stop member or the at least one second stop member of the nut member and the at least one first interaction member or the at least one second interaction member of the piston rod corresponds to the remaining amount of the drug in the cartridge.

5. The assembly according to claim 1, wherein, the assembly is configured such that, for dose delivery, axial and rotational movement of the nut member with respect to the piston rod is prevented, and wherein the nut member and the piston rod are adapted and arranged to move together in an axial direction for expelling drug from the cartridge during the dose delivery operation.

6. The assembly according to claim 1, further comprising:
a housing comprising an inner thread,
a dose setting member comprising a first thread, wherein the dose setting member is rotatably arranged within the housing due to mechanical cooperation of the inner thread and the first thread,
a clutch mechanism adapted and arranged to couple the dose setting member and the nut member during a dose setting operation such that movement of the dose setting member is transferred into axial and rotational movement of the nut member with respect to the piston rod during a dose setting operation, wherein the clutch mechanism is configured to decouple the dose setting member and the nut member for delivering the set dose such that movement of the nut member with respect to the piston rod during the dose delivery operation is prevented.

7. The assembly according to claim 6, wherein the clutch mechanism is configured such that it decouples the dose setting member and the nut member due to an operation which takes place at a beginning of a dose delivery operation.

8. The assembly according to claim 6, wherein the dose setting member comprises a second thread, and wherein the assembly further comprises a drive member comprising an engagement member adapted and arranged to mechanically cooperate with the second thread of the dose setting member, wherein the drive member is prevented from rotation with respect to the housing due to mechanical cooperation with the housing,
wherein, for setting a dose of the drug, the dose setting member is configured to be rotated in a first direction with respect to the housing and to the drive member such that the housing and the drive member are shifted at least partly out of the dose setting member due to mechanical cooperation of the housing and the drive member with the first and second threads and such that the drive member is axially moved in a first direction with respect to the housing from a first position into a second position due to mechanical cooperation of the drive member with the housing and with the dose setting member.

9. The assembly according to claim 8, wherein a displacement distance of the drive member between the first position and the second position is determined by a differences of pitches of the first and second threads.

10. The assembly according to claim 8, wherein the assembly is adapted and arranged such that a pitch of the second thread is less than a pitch of the first thread and such that the first thread and the second thread comprise the same thread direction.

11. The assembly according to claim 8, wherein the assembly is adapted and arranged such that a displacement distance of the nut member with respect to the piston rod during a dose setting operation is less than or equal to the displacement distance of the drive member between the first position and the second position during the dose setting operation.

12. The assembly according to claim 8, wherein the drive member comprises a first face and the nut member comprises a second face and wherein, for delivering a set dose of the drug, the dose setting member is configured to be rotated in a second direction with respect to the housing and to the drive member such that
the housing and the drive member are shifted at least partly back into the dose setting member and such that
the drive member is axially moved in a second direction with respect to the housing from the second position back into the first position, wherein movement of the drive member is transferred into axial movement of the nut member and the piston rod with respect to the housing for expelling the set dose out of the cartridge due to mechanical cooperation of the first face and the second face.

13. The assembly according to claim 1,
wherein an azimuthal distance between the at least one first stop member and the at least one first interaction member and an axial distance between the at least one second stop member and the at least one second interaction member correspond to the remaining amount of the drug in the cartridge, respectively.

14. The assembly according to claim 1, wherein the piston rod comprises a bearing member in contact with the bung of the cartridge.

15. The assembly according to claim 1, wherein the piston rod is configured to be fixed to the housing during the dose setting operation while the nut member rotates relative to the housing and moves proximally relative to the housing during the dose setting operation.

16. The assembly according to claim 1, wherein the at least one second stop member is distal to the at least one first stop member and protrudes proximally from the nut member.

17. A drug delivery device comprising:
a housing;
a cartridge disposed in the housing, the cartridge containing a plurality of doses of a drug;
a piston rod configured to be arranged within a housing of the drug delivery device, the piston rod adapted and arranged to transfer axial movement of the piston rod to a bung of the cartridge for expelling the drug from the cartridge during a dose delivery operation of the drug delivery device, the piston rod comprising a thread;
a nut member, wherein the nut member is adapted and arranged to be rotated with respect to the piston rod about a rotational axis during a dose setting operation of the drug delivery device, the nut member thereby being axially displaced along the piston rod from a start position towards an end position with respect to the piston rod due to mechanical cooperation of the nut member with the thread; and a last dose stop mechanism adapted and arranged to prevent a user from setting a dose of the drug which exceeds a remaining amount of drug in the cartridge, the last dose stop mechanism comprising at least one first interaction member and at least one second interaction member provided by the piston rod and at least one first stop member and at least one second stop member provided by the nut member, wherein the at least one first stop member protrudes radially inwardly from an inner surface of the nut member, and wherein the at least one first and second interaction members and the at least one first and second stop members are configured to mechanically cooperate with one another when the nut member is in the end position with respect to the piston rod such that further relative movement of the nut member and the piston rod for dose setting is prevented.

18. A drug delivery device comprising:

a housing;

a cartridge disposed in the housing, the cartridge containing a plurality of doses of a drug and the drug containing at least one pharmaceutically active compound;

a piston rod arranged within the housing, the piston rod adapted and arranged to transfer axial movement of the piston rod to a bung of the cartridge for expelling the drug from the cartridge during a dose delivery operation of the drug delivery device, the piston rod comprising a thread;

a nut member, wherein the nut member is adapted and arranged to be rotated with respect to the piston rod about a rotational axis during a dose setting operation of the drug delivery device, the nut member thereby being axially displaced along the piston rod from a start position towards an end position with respect to the piston rod due to mechanical cooperation of the nut member with the thread of the piston rod; and a last dose stop mechanism adapted and arranged to prevent a user from setting a dose of the plurality of doses of the drug which exceeds a remaining amount of the drug in the cartridge, the last dose stop mechanism comprising at least one first interaction member and at least one second interaction member provided by the piston rod and at least one first stop member and at least one second stop member provided by the nut member, wherein the at least one first stop member protrudes radially inwardly from an inner surface of the nut member, and wherein the at least one first and second interaction members and the at least one first and second stop members are configured to mechanically cooperate with one another when the nut member is in the end position with respect to the piston rod such that further relative movement of the nut member and the piston rod for dose setting is prevented.

19. A method comprising:

rotating a dose setting member of a drug delivery device to set a dose of a drug to be expelled from a cartridge of the drug delivery device by a piston rod during a delivery operation, the cartridge containing a plurality of doses of the drug comprising the dose of the drug, the piston rod being arranged within a housing of the drug delivery device and being adapted and arranged to transfer axial movement of the piston rod to a bung of the cartridge for expelling the drug from the cartridge during a dose delivery operation of the drug delivery device, the piston rod comprising a thread, wherein rotating of the dose setting member comprises rotating a nut member with respect to the piston rod about a rotational axis during a dose setting operation of the drug delivery device such that the nut member is displaced along the piston rod from a start position towards an end position with respect to the piston rod due to mechanical cooperation of the nut member with the thread of the piston rod, wherein the drug delivery device comprises a last dose stop mechanism adapted and arranged to prevent a user from setting the dose of the plurality of doses of the drug which exceeds a remaining amount of the drug in the cartridge, the last dose stop mechanism comprising at least one first interaction member and at least one second interaction member provided by the piston rod and at least one first stop member and at least one second stop member provided by the nut member, wherein the at least one first stop member protrudes radially inwardly from an inner surface of the nut member, and wherein the at least one first and second interaction members and the at least one first and second stop members are configured to mechanically cooperate with one another when the nut member is in the end position with respect to the piston rod such that further relative movement of the nut member and the piston rod for dose setting is prevented; and pushing an activation member to expel the set dose of the drug from the cartridge.

* * * * *